US011207396B2

(12) United States Patent
Orihuela et al.

(10) Patent No.: US 11,207,396 B2
(45) Date of Patent: Dec. 28, 2021

(54) IMMUNIZATION TO PROTECT AGAINST ADVERSE CARDIAC EVENTS RELATING TO PNEUMOCOCCAL INFECTION

(71) Applicant: THE BOARD OF REGENTS OF THE UNIVERSITY OF TEXAS SYSTEM, Austin, TX (US)

(72) Inventors: Carlos J. Orihuela, San Antonio, TX (US); Elaine I. Tuomanen, San Antonio, TX (US); Armand O. Brown, San Antonio, TX (US)

(73) Assignees: The Board Of Regents Of The University Of Texas System, Austin, TX (US); St. Jude Children's Research Hospital, Memphis, TN (US)

( * ) Notice: Subject to any disclaimer, the term of this patent is extended or adjusted under 35 U.S.C. 154(b) by 0 days.

(21) Appl. No.: 14/891,814

(22) PCT Filed: May 19, 2014

(86) PCT No.: PCT/US2014/038621
§ 371 (c)(1),
(2) Date: Nov. 17, 2015

(87) PCT Pub. No.: WO2014/186796
PCT Pub. Date: Nov. 20, 2014

(65) Prior Publication Data
US 2016/0101172 A1    Apr. 14, 2016

Related U.S. Application Data
(60) Provisional application No. 61/824,589, filed on May 17, 2013.

(51) Int. Cl.
*A61K 39/09* (2006.01)
*A61K 45/06* (2006.01)
*C07K 14/315* (2006.01)
*A61K 39/00* (2006.01)

(52) U.S. Cl.
CPC ............ *A61K 39/092* (2013.01); *A61K 45/06* (2013.01); *C07K 14/3156* (2013.01); *A61K 2039/6037* (2013.01); *A61K 2039/64* (2013.01); *C07K 2319/40* (2013.01)

(58) Field of Classification Search
None
See application file for complete search history.

(56) References Cited

U.S. PATENT DOCUMENTS

| 6,042,838 | A   | 3/2000  | Briles et al. ............ 424/244.1 |
| 6,232,116 | B1  | 5/2001  | Briles et al. ............ 435/320.1 |
| 6,858,706 | B2  | 2/2005  | Tuomanen et al. ......... 530/350 |
| 2001/0029251 | A1* | 10/2001 | Gonczol ............ A01K 67/0271 |
| | | | 514/44 R |
| 2009/0170162 | A1 | 7/2009 | Hollingshead et al. ..... 435/69.3 |
| 2009/0285846 | A1 | 11/2009 | Tweten ................. 424/190.1 |
| 2010/0143394 | A1* | 6/2010 | El Kasmi .......... C07K 14/3156 |
| | | | 424/190.1 |
| 2010/0166795 | A1 | 7/2010 | Mitchell et al. .......... 424/192.1 |

FOREIGN PATENT DOCUMENTS

| WO | WO 90/006951 | 6/1990 | |
| WO | WO 97/41151 | 11/1997 | |
| WO | WO 2005/108419 | 11/2005 | |
| WO | WO 2005/108580 | 11/2005 | |
| WO | WO 2008039838 A2 * | 4/2008 | ......... C07K 14/3156 |
| WO | WO-2012134975 A1 * | 10/2012 | ............. C07K 14/47 |

OTHER PUBLICATIONS

Bowie et al. (Science, 1990, 257:1306-1310).*
Greenspan et al. (Nature Biotechnology 7: 936-937, 1999).*
Bouche et al., "Induction of broadly neutralizing antibodies against measles virus mutants using a polyepitope vaccine strategy," *Vaccine*. 23, pp. 2074-2077, 2005.
Cundell et al., "Receptor specificity of adherence of *Streptococcus pneumoniae* to human type-II pneumocytes and vascular endothelial cells in vitro," *Microb Pathog*. 17, pp. 361-374, 1994.
Cundell, et al., "*Streptococcus pneumoniae* anchor to activated human cells by the receptor for platelet-activating factor," *Nature*. 377, pp. 435-438, 1995.
Daniels et al. "The proline-rich region of pneumococcal surface proteins A and C contains surface-accessible epitopes common to all pneumococci and elicits antibody-mediated protection against sepsis," *Infection and Immunity* 78, pp. 2163-2172, 2010.
El Kasmi et al., "Neutralization of measles virus wild-type isolates after immunization with a synthetic peptide vaccine which is not recognized by neutralizing passive antibodies," *J. Gen. Virol*. 81, pp. 729-735, 2000.
El Kasmi et al., "The molecular basis of virus crossreactivity and neutralisation after immunisation with optimised chimeric peptides mimicking a putative helical epitope of the measles virus hemagglutinin protein," *Mol. Immunol*. 35, pp. 905-918, 1998.
El Kasmi et al., "A hemagglutinin-derived peptide-vaccine ignored by virus-neutralizing passive antibodies, protects against murine measles encephalitis," *Vaccine*. 17, pp. 2436-2445, 1999.
Idanpaan-Heikkila, et al., "Oligosaccharides interfere with the establishment and progression of experimental pneumococcal pneumonia," *J. Infect. Dis*. 176, pp. 704-712, 1997.
International Search Report and Written Opinion issued in PCT/US14/38621, dated Oct. 8, 2014.

(Continued)

*Primary Examiner* — Robert A Zeman
(74) *Attorney, Agent, or Firm* — Womble Bond Dickinson (US) LLP

(57) ABSTRACT

In some aspects, provided herein are methods and compositions for treating or preventing adverse cardiac events in a patient who has suffered an invasive pneumococcal infection or is at risk of such an infection. The compositions include fusion proteins comprising a CbpA polypeptide or active fragment or variant thereof and optionally a T cell epitope (TCE) and a third immunogenic polypeptide from a bacteria.

7 Claims, 7 Drawing Sheets
Specification includes a Sequence Listing.

(56) References Cited

OTHER PUBLICATIONS

Jordan et al., "Three-dimensional 13C-detected CH3-TOCSY using selectively protonated proteins: facile methyl resonance assignment and protein structure determination," *J. Am. Chem. Soc.* 128(28), pp. 9119-9128, 2006.

Luo et al., "Solution structure of choline binding protein A, the major adhesin of *Streptococcus pneumoniae*," *EMBO J.* 24(1), pp. 34-43, 2005.

McDaniel, et al., "Molecular localization of variable and conserved regions of pspA and identification of additional pspA homologous sequences in *Streptococcus pneumoniae*," *Microb. Pathog.*, 13, pp. 261-269, 1992.

Obeid et al., "Protection against morbillivirus-induced encephalitis by immunization with a rationally designed synthetic peptide vaccine containing B- and T-cell epitopes from the fusion protein of measles virus," *J. Virol.* 69:1420-1428, 1995.

Orihuela et al. "Laminin receptor initiates bacterial contact with the blood brain barrier in experimental meningitis models," *J Clin Invest.*, 119(6), pp. 1638-1646, 2009.

Paton et al. "Activation of human complement by the pneumococcal toxin pneumolysin," *Infection and Immunity* 43, pp. 1085-1087, 1984.

Radin et al., "beta-Arrestin 1 participates in platelet-activating factor receptor-mediated endocytosis of *Streptococcus pneumoniae*," *Infect. Immun.* 73, pp. 7827-7835, 2005.

Ronda et al., "Biological role of the pneumococcal amidase. Cloning of the lytA gene in *Streptococcus pneumoniae*," *Eur. J. Biochem*, 164, pp. 621-624, 1987.

Saunders et al., "Pneumolysin, the thiol-activated toxin of *Streptococcus pneumoniae*, does not require a thiol group for in vitro activity," *Infection and Immunity* 57, pp. 2547-2552, 1989.

Shapiro et al. "The protective efficacy of polyvalent pneumococcal polysaccharide vaccine," *NJEM.* 325, pp. 1453-1460, 1991.

Tuomanen et al. "Pathogenesis of pneumococcal infection," *NEJM* 322, pp. 1280-1284, 1995.

Zhang et al., "The polymeric immunoglobulin receptor translocates pneumococci across human nasopharyngeal epithelial cells," *Cell.* 102, pp. 827-837, 2000.

Zysk et al. "Detection of 23 immunogenic pneumococcal proteins using convalescent-phase serum," *Infection and Immunity* 68, pp. 3740-3743, 2000.

International Preliminary Report on Patentability issued in PCT/US2014/038621, dated Nov. 26, 2015.

\* cited by examiner ical Application No. 61/824,589, filed on May 17, 2013, The entire contents of each of the above-referenced disclosures are hereby incorporated by reference.

IMMUNIZATION TO PROTECT AGAINST ADVERSE CARDIAC EVENTS RELATING TO PNEUMOCOCCAL INFECTION

CROSS-REFERENCE TO RELATED APPLICATIONS

This application is a national phase application under 35 U.S.C § 371 of International Application No. PCT/US2014/038621, filed May 19, 2014, which claims the benefit of priority of U.S. Provisional Patent Application No. 61/824,589, filed on May 17, 2013, The entire contents of each of the above-referenced disclosures are hereby incorporated by reference.

GOVERNMENTAL RIGHTS

This invention was made with government support under agreement number R21 HL108054-2 awarded by the National Institutes of Health (NIH). The government has certain rights in the invention.

BACKGROUND OF THE INVENTION

A. Field of the Invention

The invention relates to methods and compositions for treating or preventing adverse cardiac events in a patient who has suffered an invasive pneumococcal infection or are at risk of such an infection. The methods and compositions include fusion proteins useful to prevent cardiac microlesions.

B. Description of Related Art

*Streptococcus pneumoniae* is a gram positive *bacterium* which is a major cause of invasive infections such as sepsis, meningitis, otitis media and lobar pneumonia (Tuomanen et al., 1995). Infection by *S. pneumoniae* remains a significant health threat worldwide. Pneumococci bind avidly to cells of the upper and lower respiratory tract and to endothelial cells present in blood vessels.

Hospitalization for community-acquired pneumonia is frequently associated with adverse cardiac events that can lead to death; those that survive infection are at elevated risk for sudden death up to 1-year thereafter. In view of this, there remains a need for therapies that prevent adverse cardiac events in these patients.

SUMMARY OF THE INVENTION

In some aspects, provided herein are methods and compositions for treating or preventing adverse cardiac events in a patient who has suffered an invasive pneumococcal infection or who is at risk of such an infection. The compositions include proteins comprising a CbpA polypeptide or active fragment or variant thereof and optionally at least one T cell epitope (TCE) and a third immunogenic polypeptide from a bacteria.

In some embodiments, provided is a method of preventing adverse cardiac events in a patient comprising administering an effective amount of a composition to a patient, wherein the composition comprises an immunogenic polypeptide from a bacteria, wherein the patient has been identified as being at risk for developing cardiac microlesions. In some embodiments, the immunogenic polypeptide is a CbpA polypeptide or active variant or fragment thereof. In some embodiments, the immunogenic polypeptide has at least 70% sequence identity to SEQ ID NO:1, 2, 3, 6, or 7. In some embodiments, the immunogenic polypeptide comprises SEQ ID NO:1, 2, 3, 6, or 7. In some embodiments, the composition further comprises a second polypeptide. In some embodiments, the second polypeptide comprises at least one T cell epitope (TCE). In some embodiments, the second polypeptide is fused to the immunogenic polypeptide. In some embodiments, the fusion protein has at least 70% sequence identify to the amino acid sequence of SEQ ID NOs:4, 5, 8, 9, 10, 11, 12, 13, or 14. In some embodiments, the fusion protein comprises SEQ ID NOs:4, 5, 8, 9, 10, 11, 12, 13, or 14. In some embodiments, the composition comprises a fusion protein comprising a first polypeptide comprising a CbpA polypeptide or fragment thereof, a second polypeptide comprising at least one T cell epitope (TCE) fused to the first polypeptide, and a third polypeptide fused to the first or second polypeptide.

In some embodiments, the composition comprising the fusion protein prevents or reduces the formation of microlesions. In some embodiments, the composition comprising the fusion protein prevents the occurrence of an adverse cardiac event. In some embodiments, the adverse cardiac event is a myocardial infarction, reinfarction, the need for revascularization, or death.

In specific embodiments, a nucleic acid molecule may comprise a sequence which is 80, 81, 82, 83, 84, 85, 86, 87, 88, 89, 90, 91, 92, 93, 94, 95, 96, 97, 98, 99, or 100% identical (or any range derivable therein) to all or part of any of the sequences disclosed herein. In some embodiments, a nucleic acid molecule may comprise a sequence which is 80, 81, 82, 83, 84, 85, 86, 87, 88, 89, 90, 91, 92, 93, 94, 95, 96, 97, 98, 99, or 100% identical (or any range derivable therein) to a region of any of the sequences disclosed herein that has, has at most, or has at least 12, 13, 14,15, 16, 17, 18, 19, 20, 21, 22, 23, 24, 25, 26, 27, 28, 29, 30, 31, 32, 33, 34, 35, 36, 37, 38, 39, 440, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, or 125 contiguous nucleic acid residues from the sequence (or any range derivable therein). In some embodiments, the first polypeptide has at least 70% sequence identify to the amino acid sequence of SEQ ID NO:6. In some embodiments, the first polypeptide comprises SEQ ID NO:6. In some embodiments, the second polypeptide has at least 70% sequence identify to the amino acid sequence of SEQ ID NO:7. In some embodiments, the second polypeptide comprises SEQ ID NO:7. In some embodiments, the fusion protein has at least 70% sequence identify to the amino acid sequence of SEQ ID NO:8. In some embodiments, the fusion protein comprises SEQ ID NO:8.

In some embodiments, the patient has been identified as being at risk for developing cardiac microlesions based on an infection or an increased risk of infection. In some embodiments, the patient is immune deficient, is immunocompromised, is hospitalized, is undergoing an invasive medical procedure, is infected with influenza virus or is on a respirator. In some aspects the patient is not a patient having cancer, HIV or HCV infection. In some embodiments, the patient has been infected with invasive pneumococcal disease. In some embodiments, the invasive pneumococcal disease is caused by an infection with *Streptococcus pneumoniae*. In some embodiments, the method further comprises identifying the patient as having a *Streptococcus pneumoniae* infection. In some embodiments, the method further comprises selecting the patient after the patient is diagnosed with a *Streptococcus pneumoniae* infection. In some embodiments, the method further comprises testing the patient for a *Streptococcus pneumoniae* infection. In some embodiments, the method further comprises obtaining from the patient a biological sample for testing whether the patient has a *Streptococcus pneumoniae* infection. In some embodiments, the patient is at risk of a *Streptococcus pneumoniae* infection. In some embodiments, the patient is determined to have a *Streptococcus pneumoniae* infection.

The composition can be administered at any appropriate time. In some embodiments, the composition is administered within 1, 2, 3, 4, 5, 6, or 7 days of being determined to have an infection or determined as being exposed to or at risk of an infection. In some embodiments, the composition is administered within 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 hours of being determined to have an infection or determined as being exposed to or at risk of an infection.

The compositions may be administered in any appropriate manner. In some embodiments, the composition is administered orally, intraadiposally, intraarterially, intraarticularly, intracranially, intradermally, intralesionally, intramuscularly, intranasally, intraocularally, intrapericardially, intraperitoneally, intrapleurally, intraprostaticay, intrarectally, intrathecally, intratracheally, intratumorally, intraumbilically, intravaginally, intravenously, intravesicularlly, intravitreally, liposomally, locally, mucosally, orally, parenterally, rectally, subconjunctival, subcutaneously, sublingually, topically, transbuccally, transdermally, vaginally, in cremes, in lipid compositions, via a catheter, via a lavage, via continuous infusion, via infusion, via inhalation, via injection, via local delivery, via localized perfusion, bathing target cells directly, or any combination thereof.

Methods may involve administering a composition containing about, at least about, or at most about 0.001, 0.01, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 6, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%, or more (or any range or integer therein), by weight or volume of the fusion protein. In some embodiments, the composition comprising the fusion protein comprises 0.001% to 60% by weight of the fusion protein.

Methods may involve administering a composition containing about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 nanograms (ng), micrograms (mcg), milligrams (mg), or grams of a fusion protein, or any range derivable therein.

Alternatively, embodiments may involve providing or administering to the patient or to cells or tissue of the patient about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 nanograms (ng), micrograms (mcg), milligrams (mg), or grams of fusion protein, or any range derivable therein, in one dose or collectively in multiple doses. In some embodiments, the composition comprises between about 0.1 ng and about 2.0 g of a fusion protein. In some embodiments, the composition comprises the fusion protein at a concentration of 0.001 mg to 30 mg total per dose.

Alternatively, the composition may have a concentration of fusion protein that is 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 micrograms/ml or mg/ml, or any range derivable therein.

If a liquid, gel, or semi-solid composition, the volume of the composition that is administered to the patient may be about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 microliters (µl) or milliliters (ml), or any range derivable therein. In certain embodiments, the patient is administered up to about 10 ml of the composition.

The amount of fusion protein that is administered or taken by the patient may be based on the patient's weight (in kilograms). Therefore, in some embodiments, the patient is administered or takes a dose or multiple doses amounting to about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 micrograms/kilogram (kg) or mg/kg, or any range derivable therein.

The composition may be administered to (or taken by) the patient 1, 2, 3, 4, 5, 6, 7, 8, 9, 10, 11, 12, 13, 14, 15, 16, 17, 18, 19, 20 or more times, or any range derivable therein, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months, or any range derivable therein. It is specifically contemplated that the composition may be administered once daily, twice daily, three times daily, four times daily, five times daily, or six times daily (or any range derivable therein) and/or as needed to the patient. Alternatively, the composition may be administered every 2, 4, 6, 8, 12 or 24 hours (or any range derivable therein) to or by the patient. In some embodiments, the patient is administered the composition for a certain period of time or with a certain number of doses after experiencing symptoms of a pathogenic bacterial infection or being exposed to the bacteria.

In some embodiments, the method further comprises administering a second anti-microbial treatment. The second treatment can be administered in the same composition or in separate compositions. In some embodiments, the first treatment is administered, and the second treatment is administered. In some embodiments, the second treatment is administered within 3 days of the first inhibitor or treatment. In some embodiments, the second treatment is administered within 24 hours of the first treatment. In some embodiments, the second treatment is administered within 3 hours of the first treatment. In some embodiments, the second anti-microbial treatment is an antibiotic agent, an anti-infective agent, a passive vaccine or an active vaccine. In some embodiments, the interval of time between administration of composition comprising the fusion protein and the composition comprising the second active agent is 1 to 30 days.

A patient is a human patient. It is contemplated that any embodiment involving a patient may also be applied to a subject, which refers to any organism that suffers physiologically as a result from infection by *Streptococcus*. In certain embodiments, the subject is a mammal, which includes but is not limited to dogs, cats, cows, horses, pigs, monkeys, and sheep. In certain aspects, the patient is not a patient that has been determined to have cancer or that is under treatment for cancer. In some aspects, the subject is defined as a subject that has not been determined to have an HIV or HCV infection.

Unless otherwise specified, the percent values expressed herein are weight by weight and are in relation to the total composition.

The term "about" or "approximately" is defined as being close to as understood by one of ordinary skill in the art, and in one non-limiting embodiment the terms are defined to be within 10%, preferably within 5%, more preferably within 1%, and most preferably within 0.5%.

The terms "inhibiting," "reducing," "treating," or any variation of these terms, includes any measurable decrease or complete inhibition to achieve a desired result. Similarly, the term "effective" means adequate to accomplish a desired, expected, or intended result.

The terms "prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

The use of the word "a" or "an" when used in conjunction with the term "comprising" may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. in relation to the total composition.

The compositions and methods for their use can "comprise," "consist essentially of," or "consist of" any of the ingredients or steps disclosed throughout the specification. With respect to the transitional phase "consisting essentially of," in one non-limiting aspect, a basic and novel characteristic of the compositions and methods is the ability of the fusion proteins disclosed herein to treat or prevent cardiac microlesions or prevent adverse cardiac events in a patient who has been identified as being at risk for developing cardiac microlesions.

It is contemplated that any embodiment discussed in this specification can be implemented with respect to any method or composition of the invention, and vice versa. Furthermore, compositions of the invention can be used to achieve methods of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figures 1A, 1B, 1C, 1D:
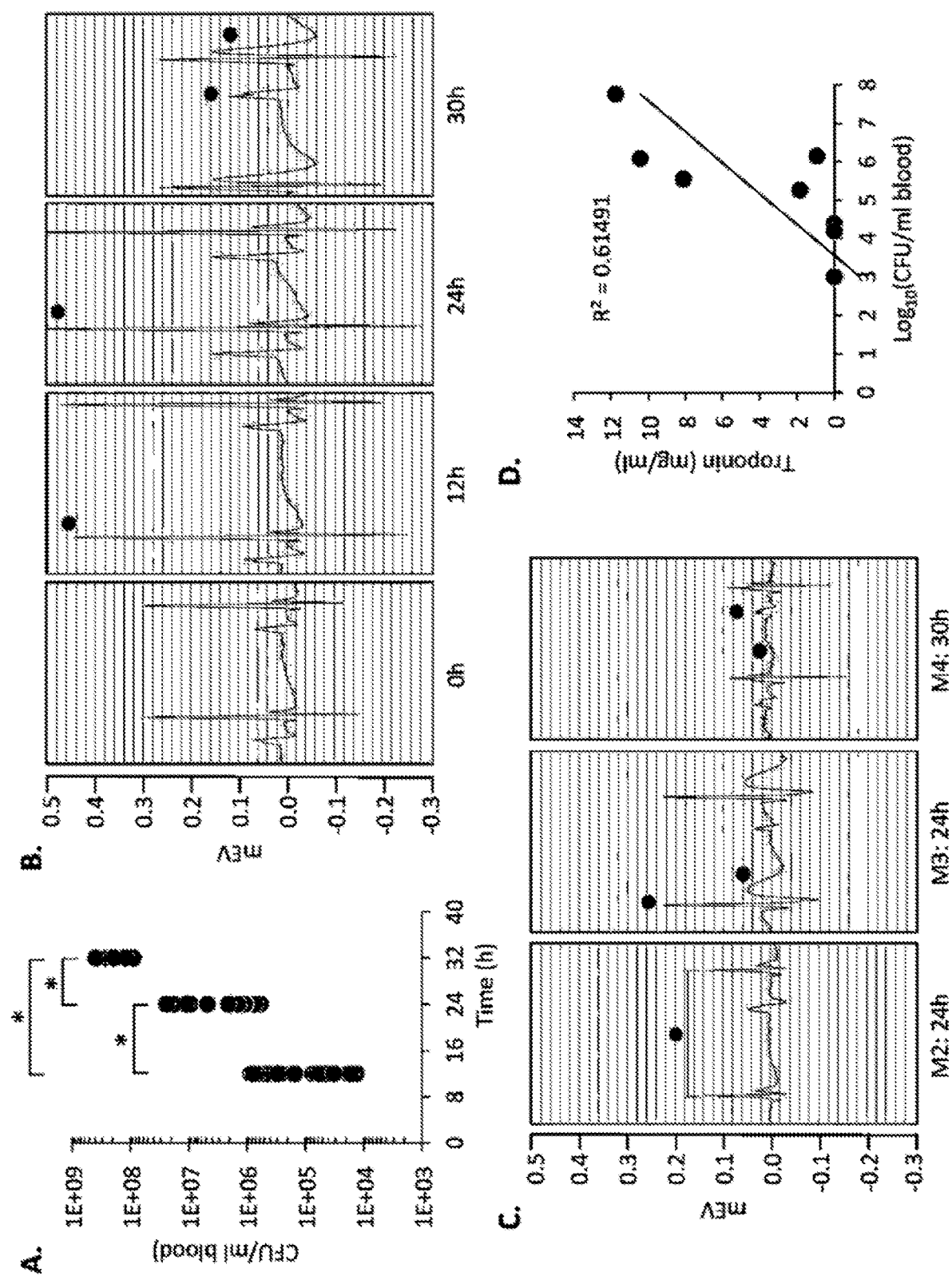
FIGS. 1A-D Invasive Pneumococcal Disease (IPD) is associated with alterations in cardiac electrophysiology and heart damage. A) Blood counts were accessed at 12 (n=24), 24 (n=17), and 30 (n=11) hours following intraperitoneal challenge with $10^3$ CFU of S. pneumoniae (strain TIGR4). Control mice were administered PBS. No bacteria were observed. Asterisks denote a statistically significant difference using a Two-tailed Student's t-test. B) Limb-lead electrocardiogram tracings of a single mouse prior to and following post intraperitoneal infection. The EKGs were acquired at 200 kHz using the 100B electrocardiogram data acquisition system (iWorx) with mice under 2% isoflurane anesthesia. C) EKG tracings obtained from 3 mice (Mouse [M] 2-4) 24-30 hours post infection highlights the variation in electrophysiology observed between septic mice. D) Quantitation of blood bacterial titers and cardiac troponin-I (cTn-I) levels 24 hours post intraperitoneal challenge with TIGR4 (n=8).

The inventors have discovered an effective therapy for treating or preventing adverse cardiac events in a patient who has been identified as being at risk for developing cardiac microlesions comprising administration of a composition comprising a fusion protein.

Hospitalization for community-acquired pneumonia is frequently associated with adverse cardiac events in 15-20% of patients that can lead to death; those that survive infection are at elevated risk for sudden death up to 1-year thereafter. These adverse cardiac events contribute to mortality. Following disease resolution, individuals hospitalized for community-acquired pneumonia are at elevated risk for death, in particular due to cardiac complications.

The inventors have discovered that *Streptococcus pneumoniae*, the leading cause of community-acquired pneumonia, causes cardiac microlesions during severe invasive pneumococcal disease. These microlesions and the scar tissue they form most likely contribute to the occurrence of adverse cardiac events as a result of altered cardiac electrophysiology. Lesion formation was positively correlated with bacterial burden in the blood as well as serum levels of troponin, a clinical marker for cardiac damage. Lesion formation was also concomitant with changes in electrophysiology, as measured by limb-lead ECG, which indicated a progressive loss of cardiac contractility. Lesions increased in number and size during the infection, becoming first detectable at 24 hours post-intravenous challenge, nonetheless remained small size in comparison to *Staphylococcus aureus* cardiac abscesses. Lesions also had a marked absence of infiltrated immune cells, which also stands in contrast to abscesses typically seen formed by other Gram-positive bacteria. Pneumococci could be visualized within the lesions and using immunohistochemistry, the toxin pneumolysin was detected at sites where apoptosis was occurring. Formation of these lesions was not bacterial strain dependent.

Immunization with the fusion proteins disclosed herein, as a stand-alone agent or as part of a multi-component vaccine, protects against formation of these previously unrecognized cardiac lesions and the long-term sequelae that are their result.

A. *STREPTOCOCCUS PNEUMONIAE*

*Streptococcus pneumoniae* is a gram positive *bacterium* which is a major cause of invasive infections such as sepsis, meningitis, otitis media and lobar pneumonia (Tuomanen et al. NEJM 322:1280-1284, 1995). Infection by *S. pneumoniae* remains a significant health threat worldwide. Pneumococci bind avidly to cells of the upper and lower respiratory tract and to endothelial cells present in blood vessels. Like most bacteria, adherence of pneumococci to human cells is achieved by presentation of bacterial surface proteins that bind to eukaryotic cell surface proteins (Cundell, D. & Tuomanen, E. (1994) Microb Pathog 17:361-374). Pneumococci bind to non-inflamed epithelium, a process that can be viewed as asymptomatic carriage. It has been proposed that the conversion to invasive disease involves the local generation of inflammatory factors which, activating the human cell, change the number and type of receptors available on the human cells (Cundell, D. et al. (1995) Nature, 377:435-438). Presented with an opportunity in this new setting, pneumococci appear to take advantage and engage one of these up-regulated receptors. For example, bacteria translocate across cells of the respiratory tract via the polymeric immunoglobulin receptor (pIgR) (Zhang et al. (2000) Cell 102:827-837). Alternatively, when the bacteria are in the blood stream, the pneumococcal bacteria bind to Laminin Receptor on endothelial cells, and the bacteria subsequently cross the blood vessel endothelium by binding to and transcytosing with the platelet activating factor (PAF) receptor (Cundell et al. (1995) Nature, 377:435-438). Within minutes of the appearance of the PAF receptor on activated cells, pneumococci undergo waves of enhanced adherence and invasion. Inhibition of bacterial binding to activated cells, for instance by soluble receptor analogs, or absence of the receptor blocks the progression to disease in animal models (Idanpaan-Heikkila, I. et al. (1997) J. Infect. Dis., 176:704-712; Radin et al. (2005) Infect. Immun. 73:7827-7835).

Pneumococci produce a family of proteins tethered to the bacterial surface by non-covalent association to the cell wall teichoic acid or lipoteichoic acid. This family of CBPs (choline binding proteins) is non-covalently bound to phosphorylcholine on the cell wall. CbpA, is a 75 kD surface-exposed choline binding protein that shows a chimeric architecture. There is a unique N-terminal domain, a proline rich region followed by a C-terminal domain comprised of 8 repeated regions responsible for binding to choline. CbpA binds specifically to pIgR on epithelial cells and Laminin receptor on diverse cell types. (Orihuela et al., 2009). When CbpA binds an extracellular domain present on pIgR, the pneumococcal bacteria are able to hijack the endocytosis machinery to translocate across nasopharyngeal epithelial cells into the blood stream. When CbpA binds to Laminin Receptor on endothelial cells this allows for translocation of the bacteria to the basolateral surface of the cell through Platelet-activating factor receptor mediated endocytosis. Mutants with defects in cbpA showed reduced virulence in the infant rat model for nasopharyngeal colonization and in mouse models of meningitis.

The choline binding domain was fully characterized by Lopez et al. in his studies of the autolytic enzyme (Ronda et al., 1987). Other proteins containing this domain include the autolysin of pneumococcus and the protective antigen, pneumococcal surface protein A (PspA) (Ronda, et al. 1987; McDaniel, et al., 1992). CbpA shares the C-terminal choline binding domain with its other family members but its activity of binding to human cells arises from its unique N-terminal domain. Since the process of colonization and the progression to disease depend on pneumococcal attachment to human cells as a primary step, interruption of the function of the N terminal domain, either by cross reactive antibody or by competitive inhibition with a peptide mimicking this domain, may be critical to blocking disease.

The N-terminus of CbpA, corresponding to amino acid residues 39-514 of the CbpA protein from the Tigr4 strain, contains numerous repeats of the leucine zipper motif that cluster within 5 domains termed the A, B, R1, R2, and C domains. The solution structure of CbpA was recently elucidated in Luo et al., 2005, which is herein incorporated by reference in its entirety. In particular, the R2 domain of CbpA (amino acid residues approximately 327 to 442) was determined to comprise three anti-parallel alpha-helices. This three alpha-helix structure is similarly predicted for R1 domain, as was recently reported in Jordan et al., 2006.

Notably, the R domains from the Tigr4 strain of *S. pneumoniae* are highly conserved among CbpA sequences from other pneumococcal strains. Therefore, the R domains of CbpA are potentially important targets for the development of vaccines that are protective against numerous pneumococcal strains. Choline binding proteins for anti-pneumococcal vaccines are discussed in U.S. Pat. No. 6,858,706 and PCT International Application No. PCT/US97/07198, both of which are incorporated in their entirety by reference. Current vaccines against *S. pneumoniae* employ purified carbohydrates of the capsules of up to the 23 most common serotypes of this *bacterium*, but such vaccines are only 50% protective against pneumonia (Shapiro et al., 1991) and are not immunogenic under the age of 2. Conjugate vaccines are based on pneumococcal capsular carbohydrates linked to diphtheria toxoid or tetanus toxoid. Protection against pneumonia, sepsis, or meningitis for these vaccines is limited to the serotypes present in the formulation, thereby leaving patients unprotected against most of the ninety-two serotypes of this *bacterium*. Further, vaccines that are protective against both the colonization of pneumococcal bacteria in the nasopharynx as well as against entry of pneumococcal bacteria into the bloodstream are needed in the art.

B. THERAPEUTIC COMPOUNDS

In some embodiments, compositions comprising a fusion protein are employed. In some embodiments the fusion protein comprises a first polypeptide comprising a CbpA polypeptide or active fragment or variant thereof, a second polypeptide comprising at least one T cell epitope (TCE) fused to the first polypeptide, and a third polypeptide fused to the first or second polypeptide, wherein the third polypeptide is from a bacteria and is immunogenic.

In some embodiments, the fusion protein is YLN. YLN is a recombinant construct composed of the pneumolysin toxoid L460D, flanked by the CbpA Laminin Receptor and Polymeric Immunoglobulin Receptor binding domains. L460D is a non-toxigenic version of the cholesterol-dependent pore-forming toxin pneumolysin. YLN is distinct from L460D in that it is flanked by fragments of the pneumococcal adhesion Choline binding protein A; one fragment having an affinity for the host cell ligand Laminin Receptor the other for Polymeric Immunoglobulin Receptor.

The Choline Binding Protein A (CbpA) contains a region of important biological activity, termed R2 (SEQ ID NO: 1) which can be subdivided into two bioactive fragments YPT (R2$_1$ region) and NEEK (R2$_2$ region). US 2010-0143394 shows how these two regions can be used as vaccines and elicit the full protection that the entire CbpA protein confers. As shown in US 2010-0143394 (FIG. 1), small peptides such as from the R2$_1$ or R2$_2$ regions are not recognized by the immune system and therefore do not generate a protective response when used alone as vaccines in a mouse model of pneumococcal infection. This is true even if the peptide is modified to be held in the appropriate folded tertiary conformation.

The immunogenicity of the fusion proteins disclosed herein can be increased through the addition of a heterologous T cell epitope (TCE). Thus, the fusion proteins disclosed herein further comprise at least one heterologous TCE fused in frame to a bacterial polypeptide or variant or fragment thereof (i.e. the CbpA polypeptide or active variant or fragment thereof). Thus, for example, an amino acid sequence for a TCE may be linked to a CbpA polypeptide or active variant or fragment thereof to increase the immunogenicity of the polypeptide relative to that of the same polypeptide lacking the TCE sequence.

As used herein, a "TCE" refers to a polypeptide sequence recognized by T cells. See, for example, El Kasmi et al., 2000; Obeid et al., 1995; El Kasmi et al., 1999; El Kasmi et al., 1998; Bouche et al., 2005. Polypeptides comprising a TCE sequence are generally between about 10-30, 30-50 or 50-90, or 90-100 amino acids, or up to a full length protein.

In some embodiments, the heterologous TCE employed in the CbpA fusion protein disclosed herein comprises an immunogenic pneumococcal polypeptide or an active variant or fragment thereof. In such embodiments, in addition to enhancing the immunogenicity of the first polypeptide by providing a TCE, employment of a second immunogenic pneumococcal polypeptide in the CbpA fusion proteins described herein provides another means to target the pneumococcal bacteria and improve immunogenicity against pneumococcal infections. Non-limiting examples of immunogenic pneumococcal proteins which can be employed in the CbpA fusion proteins disclosed herein, include, pneumolysin, pneumococcal surface protein A (PspA), neuraminidase A (nanA), β-N-acetylhexosaminidase (StrH), DnaK, or AliB protein or active variant and fragments thereof. Additional immunogenic pneumococcal polypeptides are known in the art and can be found, for example, in U.S. Pat. Nos. 6,042,838, 6,232,116, U.S. Patent Publication No. 2009/0170162A1, C. C. Daniels et al., 2010 and Zysk et al., 2000, each of which is herein incorporated by reference in their entirety.

In one embodiment, the TCE of the CbpA fusion protein comprises a pneumolysoid polypeptide or a variant or fragment thereof. Pneumolysin is a pore forming toxin and is the major cytolysin produced by *Streptococcus pneumoniae*. Pneumolysin oligomerizes to form pores in cell membranes, and facilitates intrapulmonary bacterial growth and entry into the blood stream by its hemolytic and complement activating properties. As used herein, "pneumolysoid" refers to a modified pneumolysin (a pneumolysin toxoid), wherein the modification of the protein inactivates or reduces the oligomerization, hemolytic and/or complement activating properties of the pneumolysoid protein while still retaining immunogenic activity. A reduction in the toxicity of the pneumolysin protein (i.e. a reduction in oligomerization, hemolysis, and/or complement activation) comprises at least a 1%, 5%, 10%, 20%, 30%, 40%, 50%, 60%, 70%, 80%, 90% or greater statistically significant decrease relative to an appropriate control. Various methods to assay for pneumolysin activity are known in the art. See WO 2012/134975, incorporated by reference in its entirety. Complement activation may be determined, for example, by a two-dimensional gel electrophoresis assay to detect conversion of C3. See, Paton et al., 1984, herein incorporated by reference. Oligomerization of pneumolysin may be assessed, for example, by a combination of sucrose density gradient centrifugation and gel electrophoresis as described in Saunders et al., 1989, herein incorporated by reference. Various pneumolysoids that can be employed in the various immunogenic fusion proteins provided herein are described in, for example, WO2005/108419, WO2005/108580, WO 90/06951, U.S. Patent Application No. 2009/0285846A1 and U.S. Patent Application No. 2010/0166795, which are herein incorporated by reference. WO2005/108419 and WO2005/108580 disclose pneumolysoids having a mutation (e.g. a substitution or deletion) within the region of amino acids 144 to 161 of the wild-type pneumolysin protein. These mutants have reduced oligomerization and/or hemolytic activity as compared to the wild-type pneumolysin, and are therefore less toxic. The mutant may have a substitution or deletion of one or more amino acids 144 to 161 of the wild-type pneumolysin sequence. Thus, the pneumolysoid may have a mutation at one or more of the amino acid residues 144, 145, 146, 147, 148, 149, 150, 151, 152, 153, 154, 155, 156, 157, 158, 159, 160 or 161 of wild-type pneumolysin. In addition, pneumolysoids having reduced hemolytic activity and having at least one amino acid substitution or deletion in at least one of the regions corresponding to amino acids 257-297, 367-397 or 424-437 of the wild-type pneumolysin are described in WO 90/06951.

In some embodiments, the fusion protein comprises the sequences found in Table 1.

TABLE 1

| Peptide/Protein | SEQ ID NO | Sequence |
|---|---|---|
| CbpA R2 | SEQ ID NO: 1 | MPEKKVAEAEKKVEEAKKKAEDQKEEDRRNYPTNTYKTLELEIAESDVEVKKAELELVKEEAKEPRNEEKVKQAKAEVESKKAEATRLEKIKTDRKKAEEEAKRKAAEEDKVKEKP |
| YPT$_{long}$ | SEQ ID NO: 2 | MPEKK<u>C</u>AEAEKKVEEAKKKAEDQKEEDRRNYPTNTYKTLELEIAESDVEVKKAELELV<u>C</u>EEAKE |
| NEEK$_{long}$ | SEQ ID NO: 3 | MNTY<u>C</u>TLELEIAESDVEVKKAELELVKEEAKEPRNEEKVKQAKAEVESKKAEATRLEKIKTDRKKAEEEAKRKAAEEDK<u>C</u>KEKP |
| TCE-YPT | SEQ ID NO: 4 | qyikanskfigitggA<u>C</u>KKAEDQKEEDRRNYPTNTYKTLELE<u>C</u>A |
| TCE-NEEK | SEQ ID NO: 5 | qyikanskfigitqyikanskfigitggKE<u>C</u>AKEPRNEEKVKQ<u>C</u>K |
| YPT | SEQ ID NO: 6 | MA<u>C</u>KKAEDQKEEDRRNYPTNTYKTLELE<u>C</u>AE |
| NEEK | SEQ ID NO: 7 | KE<u>C</u>AKEPRNEEKVKQ<u>C</u>K |
| YPT-L460D-NEEK(YLN) | SEQ ID NO: 8 | MA<u>C</u>KKAEDQKEEDRRNYPTNTYKTLELE<u>C</u>AEGGANKAVNDFILAMNYDKKKLLTHQGESIENRFIKEGNQLPDEFVVIERKKRSLSTNTSDISVTATNDSRLYPGALLVVDETLLENNPTLLAVDRAPMTYSIDLPGLASSDSFLQVEDPSNSSVRGAVNDLLAKWHQDYGQVNNVPARMQYEKITAHSMEQLKVKFGSDFEKTGNSLDIDFNSVHSGEKQIQIVNFKQIYYTVSVDAVKNPGDVFQDTVTVEDLKQRGISAERPLVYISSVAYGRQVYLKLETTSKSDEVEAAFEALIKGVKVAPQTEWKQILDNTEVKAVILGGDPSSGARVVTGKVDMVEDLIQEGSRFTADHPGLPISYTTSFLRDNVVATFQNSTDYVETKVTAYRNGDLLLDHSGAYVAQYYITWDELSYDHQGKEVLTPKAWDRNGQDLTAHFTTSIPLKGNVRNLSVKIRECTGLAWEWWRTVYEKTDLPLVRKRTISIWGTTDYPQVEDKVENDKE<u>C</u>AKEPRNEEKVKQ<u>C</u>K |
| YPT-Δ6D385N-NEEK | SEQ ID NO: 9 | MA<u>C</u>KKAEDQKEEDRRNYPTNTYKTLELE<u>C</u>AEGGANKAVNDFILAMNYDKKKLLTHQGESIENRFIKEGNQLPDEFVVIERKKRSLSTNTSDISVTATNDSRLYPGALLVVDETLLENNPTLLAVDRAPMTYSIDLPGLASSDSFLQVEDPSNSSVRGAVNDLLAKWHQDYGQVNNVPMQYEKITAHSMEQLKVKFGSDFEKTGNSLDIDFNSVHSGEKQIQIVNFKQIYYTVSVDAVKNPGDVFQDTVTVEDLKQRGISAERPLVYISSVAYGRQVYLKLETTSKSDEVEAAFEALIKGVKVAPQTEWKQILDNTEVKAVILGGDPSSGARVVTGKVDMVEDLIQEGSRFTADHPGLPISYTTSFLRDNVVATFQNSTDYVETKVTAYRNGDLLLDHSGAYVAQYYITWDELSYNHQGKEVLTPKAWDRNGQDLTAHFTTSIPLKGNVRNLSVKIRECTGLAWEWWRTVYEKTDLPLVRKRTISIWGTTLYPQVEDKVENDKE<u>C</u>AKEPRNEEKVKQ<u>C</u>K |
| YPT-PdT-NEEK | SEQ ID NO: 10 | MA<u>C</u>KKAEDQKEEDRRNYPTNTYKTLELE<u>C</u>AEGGANKAVNDFILAMNYDKKKLLTHQGESIENRFIKEGNQLPDEFVVIERKKRSLSTNTSDISVTATNDSRLYPGALLVVDETLLENNPTLLAVDRAPMTYSIDLPGLASSDSFLQVEDPSNSSVRGAVNDLLAKWHQDYGQVNNVPARMQYEKITAHSMEQLKVKFGSDFEKTGNSLDIDFNSVHSGEKQIQIVNFKQIYYTVSVDAVKNPGDVFQDTVTVEDLKQRGISAERPLVYISSVAYGRQVYLKLETTSKSDEVEAAFEALIKGVKVAPQTEWKQILDNTEVKAVILGGDPSSGARVVTGKVDMVEDLIQEGSRFTADHPGLPISYTTSFLRDNVVATFQNSTDYVETKVTAYRNGDLLLDHSGAYVAQYYITWDELSYNHQGKEVLTPKAWDRNGQDLTAHFTTSIPLKGNVRNLSVKIREGTGLAFEWWRTVYEKTDLPLVRKRTISIWGTTLYPQVEDKVENDKE<u>C</u>AKEPRNEEKVKQ<u>C</u>K |
| YPT-L460D | SEQ ID NO: 11 | MA<u>C</u>KKAEDQKEEDRRNYPTNTYKTLELE<u>C</u>AEGGANKAVNDFILAMNYDKKKLLTHQGESIENRFIKEGNQLPDEFVVIERKKRSLSTNTSDISVTATNDSRLYPGALLVVDETLLENNPTLLAVDRAPMTYSIDLPGLASSDSFLQVEDPSNSSVRGAVNDLLAKWHQDYGQVNNVPARMQYEKITAHSMEQLKVKFGSDFEKTGNSLDIDFNSVHSGEKQIQIVNFKQIYYTVSVDAVKNPGDVFQDTVTVEDLKQRGISAERPLVYISSVAYGRQVYLKLETTSKSDEVEAAFEALIKGVKVAPQTEWKQILDNTEVKAVILGGDPSSGARVVTGKVDMVEDLIQEGSRFTADHPGLPISYTTSFLRDNVVATFQNSTDYVETKVTAYRNGDLLLDHSGAYVAQYYITWDELSYDHQGKEVLTPKAWDRNGQDLTAHFTTSIPLKGNVRNLSVKIRECTGLAWEWWRTVYEKTDLPLVRKRTISIWGTTDYPQVEDKVEND |
| L460D-NEEK | SEQ ID NO: 12 | MANKAVNDFILAMNYDKKKLLTHQGESIENRFIKEGNQLPDEFVVIERKKRSLSTNTSDISVTATNDSRLYPGALLVVDETLLENNPTLLAVDRAPMTYSIDLPGLASSDSFLQVEDPSNSSVRGAVNDLLAK |

TABLE 1-continued

| Peptide/Protein | SEQ ID NO | Sequence |
|---|---|---|
| | | WHQDYGQVNNVPARMQYEKITAHSMEQLKVKFGSDFEKTGNS
LDIDFNSVHSGEKQIQIVNFKQIYYTVSVDAVKNPGDVFQDTVT
VEDLKQRGISAERPLVYISSVAYGRQVYLKLETTSKSDEVEAAFE
ALIKGVKVAPQTEWKQILDNTEVKAVILGGDPSSGARVVTGKV
DMVEDLIQEGSRFTADHPGLPISYTTSFLRDNVVATFQNSTDYVE
TKVTAYRNGDLLLDHSGAYVAQYYITWDELSYDHQGKEVLTP
KAWDRNGQDLTAHFTTSIPLKGNVRNLSVKIRECTGLAWEWW
RTVYEKTDLPLVRKRTISIWGTTDYPQVEDKVENDKE<u>C</u>AK**EPR
NEEK**VKQ<u>C</u>K |
| YPT-PdT | SEQ ID NO: 13 | MA<u>C</u>KKAEDQKEEDRRNYPTNTYKTLELE<u>C</u>AEGGANKAVNDFI
LAMNYDKKKLLTHQGESIENRFIKEGNQLPDEFVVIERKKRSLST
NTSDISVTATNDSRLYPGALLVVDETLLENNPTLLAVDRAPMTY
SIDLPGLASSDSFLQVEDPSNSSVRGAVNDLLAKWHQDYGQVN
NVPARMQYEKITAHSMEQLKVKFGSDFEKTGNSLDIDFNSVHSG
EKQIQIVNFKQIYYTVSVDAVKNPGDVFQDTVTVEDLKQRGISA
ERPLVYISSVAYGRQVYLKLETTSKSDEVEAAFEALIKGVKVAP
QTEWKQILDNTEVKAVILGGDPSSGARVVTGKVDMVEDLIQEG
SRFTADHPGLPISYTTSFLRDNVVATFQNSTDYVETKVTAYRNG
DLLLDHSGAYVAQYYITWDELSYNHQGKEVLTPKAWDRNGQD
LTAHFTTSIPLKGNVRNLSVKIREGTGLAFEWWRTVYEKTDLPL
VRKRTISIWGTTLYPQVEDKVEND |
| PdT-NEEK | SEQ ID NO: 14 | MANKAVNDFILAMNYDKKKLLTHQGESIENRFIKEGNQLPDEFV
VIERKKRSLSTNTSDISVTATNDSRLYPGALLVVDETLLENNPTL
LAVDRAPMTYSIDLPGLASSDSFLQVEDPSNSSVRGAVNDLLAK
WHQDYGQVNNVPARMQYEKITAHSMEQLKVKFGSDFEKTGNS
LDIDFNSVHSGEKQIQIVNFKQIYYTVSVDAVKNPGDVFQDTVT
VEDLKQRGISAERPLVYISSVAYGRQVYLKLETTSKSDEVEAAFE
ALIKGVKVAPQTEWKQILDNTEVKAVILGGDPSSGARVVTGKV
DMVEDLIQEGSRFTADHPGLPISYTTSFLRDNVVATFQNSTDYVE
TKVTAYRNGDLLLDHSGAYVAQYYITWDELSYNHQGKEVLTP
KAWDRNGQDLTAHFTTSIPLKGNVRNLSVKIREGTGLAFEWWR
TVYEKTDLPLVRKRTISIWGTTLYPQVEDKVENDKE<u>C</u>AK**EPRNE
EK**VKQ<u>C</u>K |

C. PHARMACEUTICAL PREPARATIONS

Certain methods and compositions set forth herein are directed to administration of an effective amount of a composition comprising the the fusion protein compositions of the present invention.

1. Compositions

A "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (Remington's, 1990). Except insofar as any conventional carrier is incompatible with the active ingredient, its use in the therapeutic or pharmaceutical compositions is contemplated. The compositions used in the present invention may comprise different types of carriers depending on whether it is to be administered in solid, liquid or aerosol form, and whether it needs to be sterile for such routes of administration as injection.

The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions, and these are discussed in greater detail below. For human administration, preparations should meet sterility, pyrogenicity, general safety and purity standards as required by FDA Office of Biologics standards.

The formulation of the composition may vary depending upon the route of administration. For parenteral administration in an aqueous solution, for example, the solution should be suitably buffered if necessary and the liquid diluent first rendered isotonic with sufficient saline or glucose. In this connection, sterile aqueous media that can be employed will be known to those of skill in the art in light of the present disclosure.

In addition to the compounds formulated for parenteral administration, such as intravenous or intramuscular injection, other pharmaceutically acceptable forms include, e.g., tablets or other solids for oral administration; liposomal and nanoparticle formulations; enteric coating formulations; time release capsules; formulations for administration via an implantable drug delivery device, and any other form. One may also use nasal solutions or sprays, aerosols or inhalants in the present invention.

The capsules may be, for example, hard shell capsules or soft-shell capsules. The capsules may optionally include one or more additional components that provide for sustained release.

In certain embodiments, pharmaceutical composition includes at least about 0.1% by weight of the active compound. In other embodiments, the pharmaceutical composition includes about 2% to about 75% of the weight of the composition, or between about 25% to about 60% by weight of the composition, for example, and any range derivable therein.

The compositions may comprise various antioxidants to retard oxidation of one or more components. Additionally, the prevention of the action of microorganisms can be accomplished by preservatives such as various antibacterial and antifungal agents, including but not limited to parabens (e.g., methylparabens, propylparabens), chlorobutanol, phenol, sorbic acid, thimerosal or combinations thereof. The composition should be stable under the conditions of manufacture and storage, and preserved against the contaminating action of microorganisms, such as bacteria and fungi.

In certain preferred embodiments, an oral composition may comprise one or more binders, excipients, disintegration agents, lubricants, flavoring agents, and combinations thereof. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

In particular embodiments, prolonged absorption can be brought about by the use in the compositions of agents delaying absorption, such as, for example, aluminum monostearate, gelatin, or combinations thereof.

2. Routes of Administration

Upon formulation, solutions will be administered in a manner compatible with the dosage formulation and in such amount as is therapeutically effective.

The composition can be administered to the subject using any method known to those of ordinary skill in the art. For example, a pharmaceutically effective amount of the composition may be administered intravenously, intracerebrally, intracranially, intraventricularly, intrathecally, into the cortex, thalamus, hypothalamus, hippocampus, basal ganglia, substantia nigra or the region of the substantia nigra, cerebellum, intradermally, intraarterially, intraperitoneally, intralesionally, intratracheally, intranasally, topically, intramuscularly, intraperitoneally, anally, subcutaneously, orally, topically, locally, inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (Remington's, 1990).

In particular embodiments, the composition is administered to a subject using a drug delivery device. Any drug delivery device is contemplated for use in delivering an effective amount of the fusion protein.

3. Dosage

A pharmaceutically effective amount of the fusion protein is determined based on the intended goal. The quantity to be administered, both according to number of treatments and dose, depends on the subject to be treated, the state of the subject, the protection desired, and the route of administration. Precise amounts of the therapeutic agent also depend on the judgment of the practitioner and are peculiar to each individual.

The amount of the fusion protein to be administered will depend upon the disease to be treated, the length of duration desired and the bioavailability profile of the implant, and the site of administration. Generally, the effective amount will be within the discretion and wisdom of the patient's physician. Guidelines for administration include dose ranges of from about 0.01 mg to about 500 mg of the fusion protein.

For example, a dose of the fusion protein may be about 0.0001 milligrams to about 1.0 milligrams, or about 0.001 milligrams to about 0.1 milligrams, or about 0.1 milligrams to about 1.0 milligrams, or even about 10 milligrams per dose or so. Multiple doses can also be administered. In some embodiments, a dose is at least about 0.0001 milligrams. In further embodiments, a dose is at least about 0.001 milligrams. In still further embodiments, a dose is at least 0.01 milligrams. In still further embodiments, a dose is at least about 0.1 milligrams. In more particular embodiments, a dose may be at least 1.0 milligrams. In even more particular embodiments, a dose may be at least 10 milligrams. In further embodiments, a dose is at least 100 milligrams or higher.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

The dose can be repeated as needed as determined by those of ordinary skill in the art. Thus, in some embodiments of the methods set forth herein, a single dose is contemplated. In other embodiments, two or more doses are contemplated. In some embodiments, the two or more doses are the same dosage. In some embodiments, the two or more doses are different dosages. Where more than one dose is administered to a subject, the time interval between doses can be any time interval as determined by those of ordinary skill in the art. For example, the time interval between doses may be about 1 hour to about 2 hours, about 2 hours to about 6 hours, about 6 hours to about 10 hours, about 10 hours to about 24 hours, about 1 day to about 2 days, about 1 week to about 2 weeks, or longer, or any time interval derivable within any of these recited ranges. In specific embodiments, the composition may be administered daily, weekly, monthly, annually, or any range therein.

In certain embodiments, it may be desirable to provide a continuous supply of a pharmaceutical composition to the patient. This could be accomplished by catheterization, followed by continuous administration of the therapeutic agent. The administration could be intra-operative or post-operative.

4. Secondary and Combination Treatments

Certain embodiments provide for the administration or application of one or more secondary or additional forms of therapies. The type of therapy is dependent upon the type of disease that is being treated or prevented. The secondary form of therapy may be administration of one or more secondary pharmacological agents that can be applied in the treatment or prevention of intestinal polyps or cancer or a disease, disorder, or condition associated with intestinal polyps and cancer in a patient who has been identified as being at risk for developing intestinal polyps or intestinal cancer.

If the secondary or additional therapy is a pharmacological agent, it may be administered prior to, concurrently, or following administration of the fusion protein.

The interval between administration of the fusion protein and the secondary or additional therapy may be any interval as determined by those of ordinary skill in the art. For example, the fusion protein and the secondary or additional therapy may be administered simultaneously, or the interval between treatments may be be minutes to weeks. In embodiments where the agents are separately administered, one would generally ensure that a significant period of time did not expire between the time of each delivery, such that each therapeutic agent would still be able to exert an advantageously combined effect on the subject. For example, the interval between therapeutic agents may be about 12 h to about 24 h of each other and, more preferably, within about 6 hours to about 12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. In some embodiments, the timing of administration of a secondary therapeutic agent is determined based on the response of the subject to the fusion protein.

D. THERAPEUTIC METHODS

In some embodiments, methods of preventing adverse cardiac events in a patient comprising administering an effective amount of a composition comprising to a patient who has been identified as being at risk for developing cardiac microlesions are provided.

"Treatment" and "treating" refer to administration or application of a therapeutic agent to a subject or performance of a procedure or modality on a subject for the purpose of obtaining a therapeutic benefit for a disease or health-related condition.

The terms "therapeutic benefit," "therapeutically effective," or "effective amount" refer to the promotion or enhancement of the well-being of a subject. This includes, but is not limited to, a reduction in the frequency or severity of the signs or symptoms of a disease.

"Prevention" and "preventing" are used according to their ordinary and plain meaning. In the context of a particular disease or health-related condition, those terms refer to administration or application of an agent, drug, or remedy to a subject or performance of a procedure or modality on a subject for the purpose of preventing or delaying the onset of a disease or health-related condition.

E. COMBINATION THERAPY

The compositions and related methods of the present invention, particularly administration of the fusion protein, may also be used in combination with the administration of traditional therapies. These include, but are not limited to, the administration of vaccines; anti-bacterial antibodies; or antibiotics such as streptomycin, ciprofloxacin, doxycycline, gentamycin, chloramphenicol, trimethoprim, sulfamethoxazole, ampicillin, tetracycline or various combinations of antibiotics.

In one aspect, it is contemplated that the fusion protein therapy is used in conjunction with other antibacterial treatment. Alternatively, the therapy may precede or follow the other agent treatment by intervals ranging from minutes to weeks. In embodiments where the other agents and/or a proteins or polynucleotides are administered separately, one would generally ensure that a significant period of time did not expire between the time of each delivery, such that the agent and antigenic composition would still be able to exert an advantageously combined effect on the subject. In such instances, it is contemplated that one may administer both modalities within about 12-24 h of each other or within about 6-12 h of each other. In some situations, it may be desirable to extend the time period for administration significantly, where several days (2, 3, 4, 5, 6 or 7) to several weeks (1, 2, 3, 4, 5, 6, 7 or 8) lapse between the respective administrations.

Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

F. EXAMPLES

The following examples are included to demonstrate certain non-limiting aspects of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention.

Example 1

Invasive Pneumococcal Disease (IPD) is Associated with Alterations in Cardiac Electrophysiology and Heart Damage To assess whether alterations in cardiac function occurred during IPD, the inventors performed limb-lead EKGs on BALB/c mice following intraperitoneal challenge with *S. pneumoniae* serotype 4, strain TIGR4. This strain and infection route resulted in a steady and significant increase in bacterial burden from 12 to 30 hours (FIG. 1A), after which the mice became severely moribund and died. EKG tracings from these mice showed progressive and aberrant changes in cardiac electrophysiology (FIG. 1B). More specifically, signs of prolonged ventricular contraction and/or atrial fibrillation were obvserved; this included chaotic conduction of electrical signals, elongated QRS intervals, elevated ST intervals, and bifurcated P-waves. In most instances the presence of a J-wave was observed that was indicative of sepsis-associated hypothermia; the latter confirmed by the detection of reduced core body temperature at 30 hours. Importantly, the specific EKG abnormalities observed varied between individual mice (FIG. 1C). A positive correlation between bacterial burden in the blood and cardiac troponin, a marker for heart damage in sera, was observed for infected mice (FIG. 1D). In an electronic review of patient records, cardiac troponin was also found to be elevated in human serum samples from 16 of 23 (67%) patients admitted to the VA hospital in San Antonio, Tex. with confirmed IPD. There was also a strong trend towards in-hospital mortality for individuals with elevated troponin levels (P=0.076). Thus, severe IPD altered cardiac function, incurred cardiomyocyte damage, and possibly contributed towards death.

Example 2

Cardiac Lesions Form as the Result of IPD

Figures 2A, 2B, 2C, 2D, 2E, 2F, 2G, 2H, 2I, 2J:
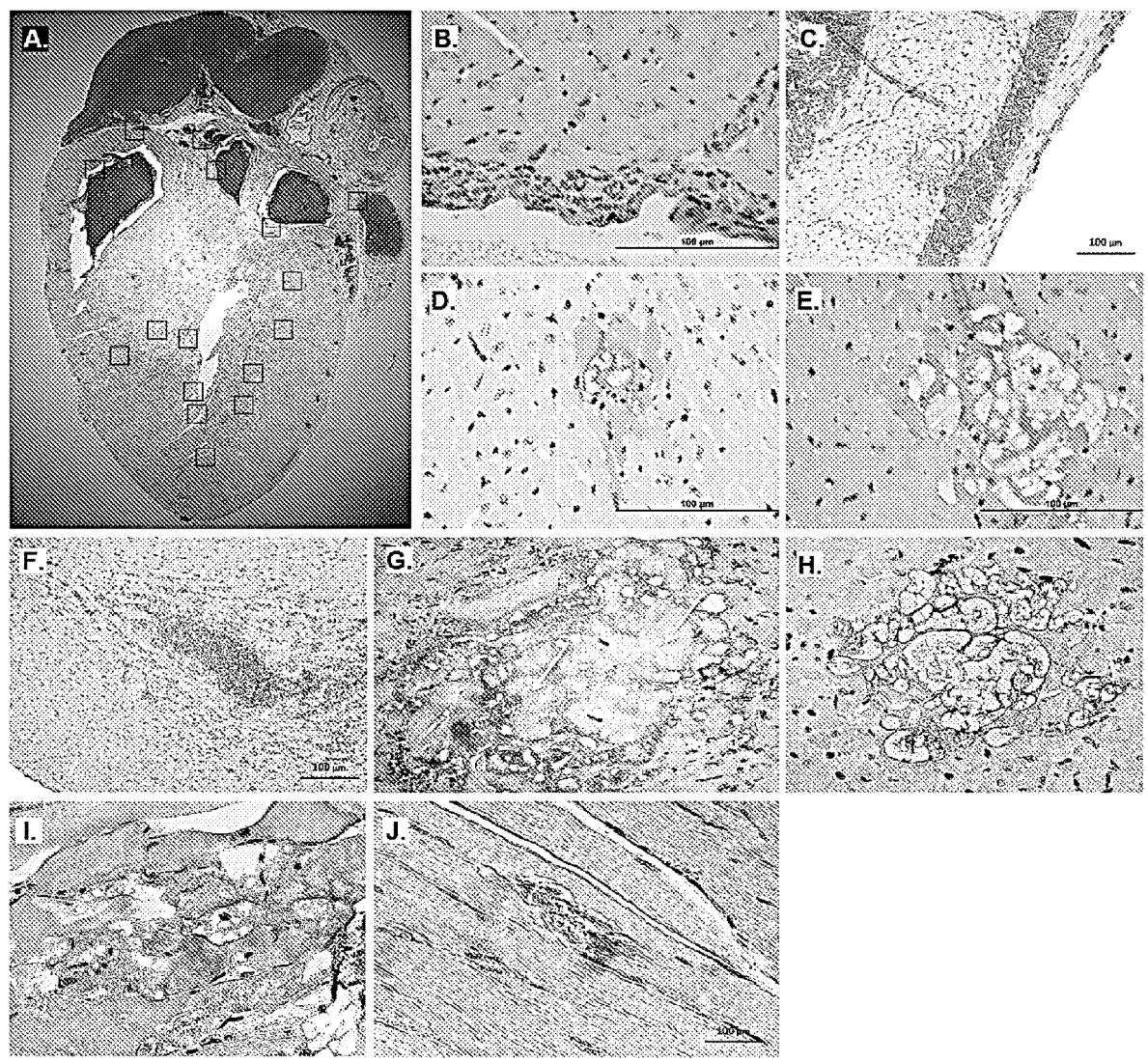
FIGS. 2A-J Hematoxylin and Eosin (H&E) stained cross section of a heart obtained from a mouse 30 hours post-intraperitoneal challenge with S. pneumoniae strain TIGR4. A) Cardiac microlesions are randomly distributed throughout mouse myocardium. B) Pericarditis is also regularly observed in these mice at 30 hours post infection. C) A relatively rare cardiac microlesion adjacent to cardiac blood vessel. D) Representative cardiac microlesion seen at 24 (n=6) and E) 30 (n=6) hours post infection. F) As a point of contrast a cardiac abscess formed in mice infected with Staphylococcus aureus 4 days post infection. G) Higher powered magnification of a S. pneumoniae cardiac lesion formed 30 hours post-infection. Arrows denote granular bodies with diplococci morphology. H) Gram stain of cardiac lesion formed 30 hours post-infection. I) Lesion found in the calf of mice 30 hours post-infection with TIGR4. J) Cardiac lesion also observed in SIV infected Rhesus macaque that succumb to infection with Streptococcus pneumoniae (Serotype 19F).

When hearts from BALB/c mice with severe IPD, both the result of intratracheal and intraperitoneal challenge with TIGR4, were examined for pathology. The pericarditis was observed, and also the presence of randomly distributed microlesions throughout the myocardium (FIG. 2A-B). In the majority of instances microlesions were not immediately adjacent to cardiac blood vessels suggesting some form of cardiac tissue invasion. Lesions were characterized by vacuolation, the apparent loss of cardiomyocytes, and a general absence of infiltrated immune cells within the lesion and in the surrounding tissue (FIG. 2C-E). Importantly, these microlesions were highly distinct from those observed following experimental challenge with *S. aureus* (FIG. 2F), a common cause of tissue and cardiac abscesses, being much smaller in size and lacking the prolific infiltration of neutrophils. Granular bodies with a diplococcus morphology could be seen within fully formed lesions in the H&E stained sections (FIG. 2G). These were confirmed to be *S. pneumoniae* by Gram-stain (FIG. 2H). In general the number and size of these abscesses increased dramatically from 24 to 30 hours post-infection (FIGS. D, E); the time point when mice had ~$10^{5-6}$ and $10^{7-8}$ CFU/ml in their blood, respectively. Microlesions were undetectable prior to 24 hour following intravenous challenge. Microlesion formation was also observed in BALB/c and C57BL/6 mice infected with *S. pneumoniae* strain D39 (serotype 2), and A66.1 (serotype 3). Thus, formation of microlesions was neither mouse strain nor bacterial strain dependent. Similar microlesions were not observed in the kidneys, livers and spleens of mice with confirmed cardiac lesions (n=12); albeit they were detected at a much lower frequency in calf muscle from infected mice at 30 hours suggesting this phenomenon may be restricted to myocytes (FIG. 2E). In the murine calf muscle, bacteria within myocytes were observed, which was never observed in the cardiac microlesions, Finally, microlesions were observed in 1 of 2 cardiac sections obtained from highly active antiretroviral therapy (HAART)-treated SIV infected *rhesus macaques* that had succumbed to experimental challenge with *S. pneumoniae* serotype 19F (FIG. 2I). Thus, direct damage to the heart was seen via microlesion formation occurred during fulminate pneumococcal infection in a manner that was strain and species independent.

Example 3

Figures 3A, 3B, 3C:
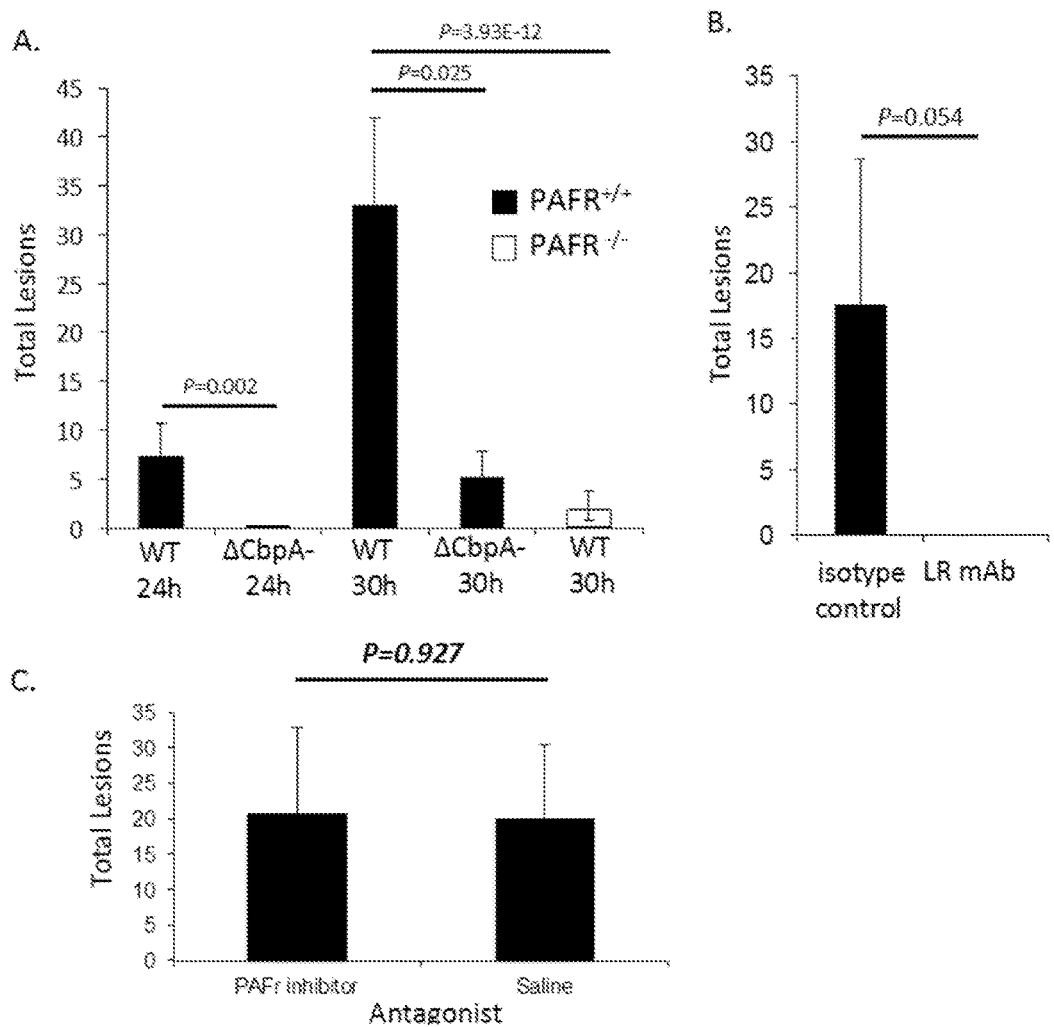
FIGS. 3A-C Lesion formation is dependent on the host protein PAFr and the bacterial adhesin CbpA. A) Wild-type BALB/c mice (n=6) were challenged with S. pneumoniae strain TIGR4 (WT) or TIGR4ΔCbpA (CbpA-). Hearts were removed 24 and 30 hours following intraperitoneal infection, sectioned, and stained with H&E. Cardiac lesions were counted across the entire section. The infection was repeated using PAFr-deficient mice (n=18). Significant reduction in cardiac lesion formation illustrates the requirement for CbpA and host PAFr in cardiac lesion formation. Lesion counts were analyzed using the Student's t-test. B) Comparison of cardiac lesions in mice 30 hours post infection following administration of 40 μg of the isotype control or anti-Lamin Receptor (LR) monoclonal antibody prior to challenge with TIGR4 indicates that the CbpA/LR is required for microlesion formation (n=4). Statistical analysis was performed using a Student's t-test. C) Treatment of mice prior to infection with the PAFr antagonist BN 52021 (ginkolide B) had no effect on cardiac mirolesion formation. Statistical analysis was performed using a Student's t-test.

Lesion Formation is Dependent the Host Protein PAFr and the Bacterial Adhesin CbpA Pneumococcal translocation across the blood brain barrier requires the bacterial adhesin CbpA, which binds to LR on vascular endothelial cells, as well as ChoP that binds to host cell PAFr. Along such lines, the inventorssought to determine whether pneumococcal invasion into the myocardial tissue occurred through the same mechanisms. Using CbpA and PAFr deficient bacteria and mice, respectively, the inventors observed an absolute requirement for these proteins in cardiac microlesion formation (FIG. 3A). When passively administered to mice prior to infection monoclonal antibodies against LR also completed blocked lesion formation (FIG. 3B). In contrast treatment of mice with a PAFr antagonist had no effect (FIG. 3C). Passive administration of mouse monoclonal antibodies against the LR binding domain of CbpA and rabbit polyclonal antisera against intact CbpA were also ineffective (FIG. 3B). Thus, bacterial invasion into the heart was indeed CbpA/LR and PAFr dependent and could, but with limited success, be blocked with existing reagents. Of note, cardiac microlesions were detected in TLR2 and TNFα deficient mice. Thus, bacterial translocation into the heart was independent of TLR2 binding; moreover, this phenomenon was most likely independent of the concurrent sepsis syndrome being experienced by the infected mice.

Example 4

Cardiac Lesions are Associated with Pneumolysin

Figures 4A, 4B, 4C:
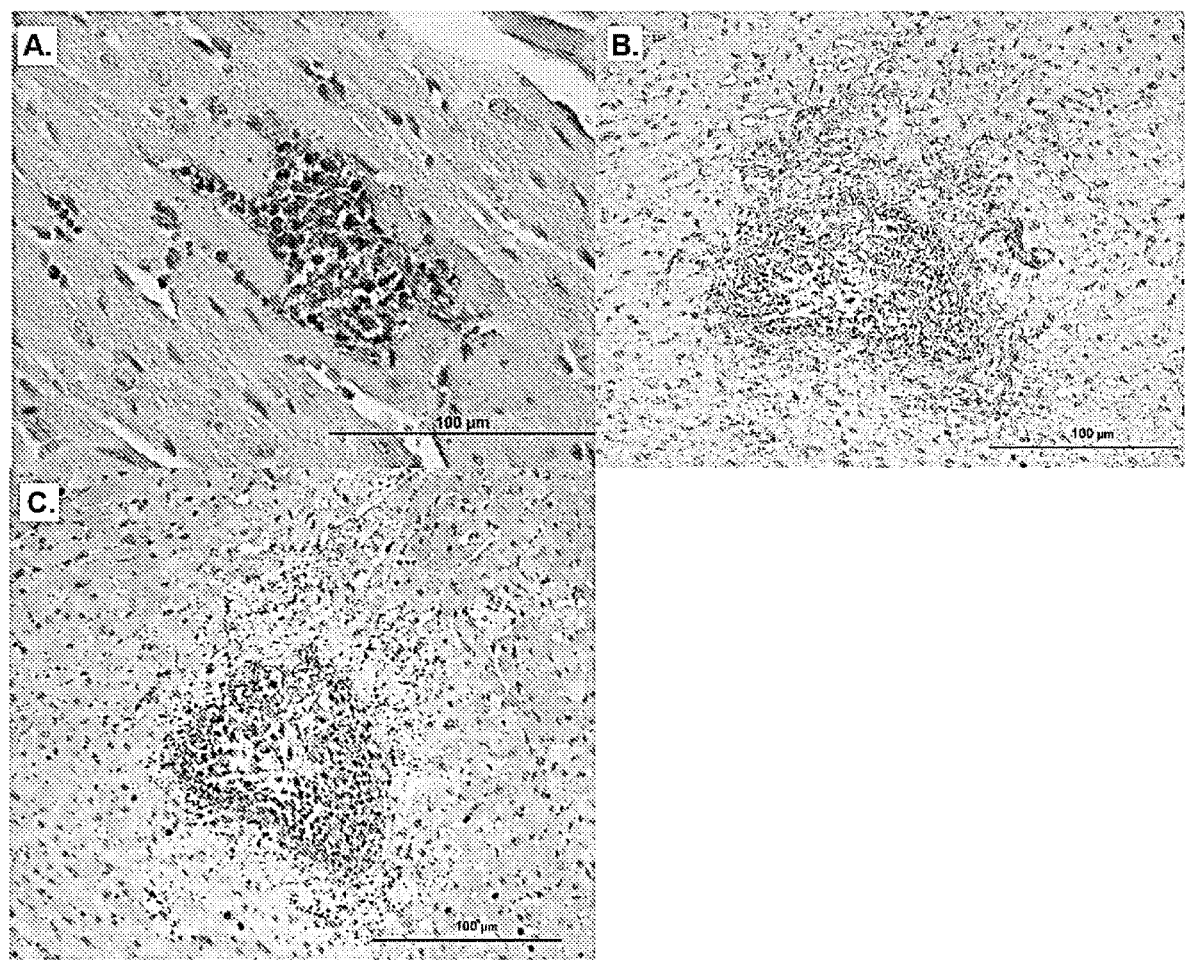
FIGS. 4A-C Cardiac lesions are occurring as a result of IL-1 induced pyroaptosis. A) TUNEL staining of a heart section from a septic mouse infected with TIGR4 indicates apoptotic activity at site of abscess. Immunohistochemical analysis highlights the presence of concentrated B) IL-1β and C) pneumolysin at microlesions.

TUNEL staining for fragmented DNA confirmed the presence of dying cells along the periphery of the lesions (FIG. 4A), likewise we confirmed the presence of IL-1b at the lesion site (FIG. 4B) suggesting that the inflammasome had been activated. This was consistent with our detection of the pore-forming toxin pneumolysin, which is known to activate the inflammasome, by immunohistochemistry at the lesion site (FIG. 4C). Notably, injection of mice with a bolus of pneumolysin, purified cell wall, or both failed to result in lesion formation after 24 hours; indicating that cardiomyocyte invasion was requisite.

Example 5

YLN Immunized Mice are Protected Against Lesion Formation

Figures 5A, 5B:
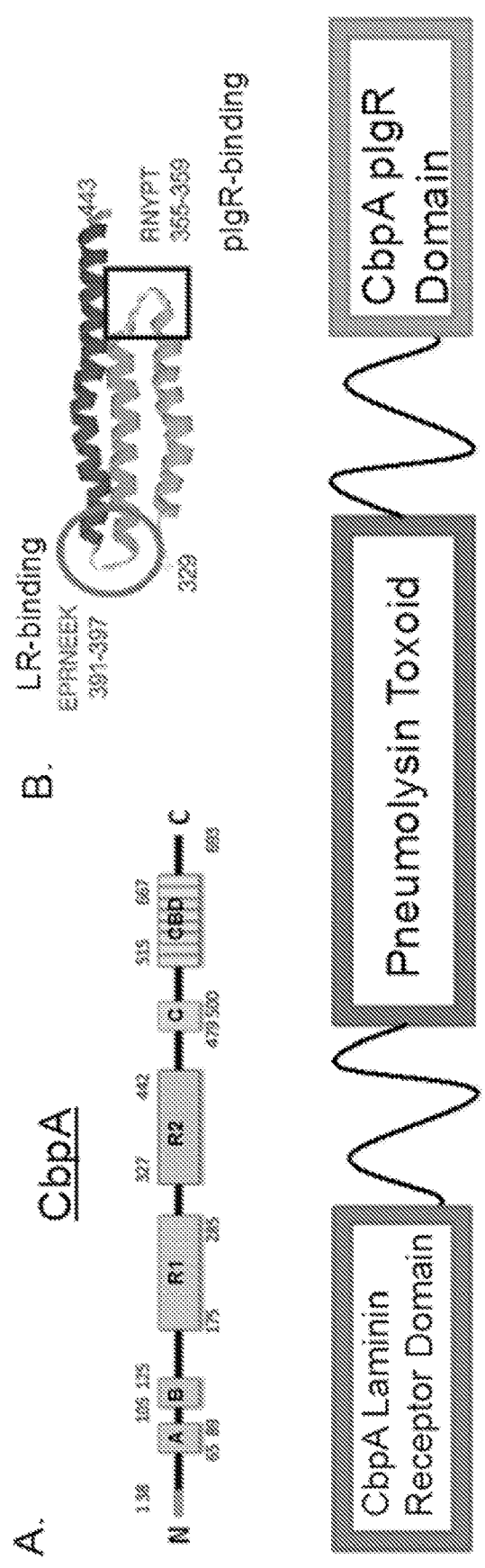
FIGS. 5A-D YLN immunized mice are protected against lesion formation. A) Domain map of the CbpA protein indicates that this protein consists of 6 Domains with an identical R1 and R2 domain, and choline binding domain located near the C-terminus. B) Ribbon structure of CbpA R2 domain indicates that the R1 and R2 domains are composed of antiparallel helices. R1 and R2 domains of CbpA contain sequence conserved loops between the helices that are required for binding laminin receptor and polymeric immunoglobulin receptor. YLN is a recombinant construct composed of the pneumolysin toxoid L460D, flanked by the CbpA Laminin Receptor and Polymeric Immunoglobulin Receptor binding domains. C) Blood from immunized mice was quantitated 24 hours following challenge with TIGR4. D) YLN is protective against cardiac lesion formation (n=5). Statistical analysis was performed using a Student's t-test.
Figure 5C:
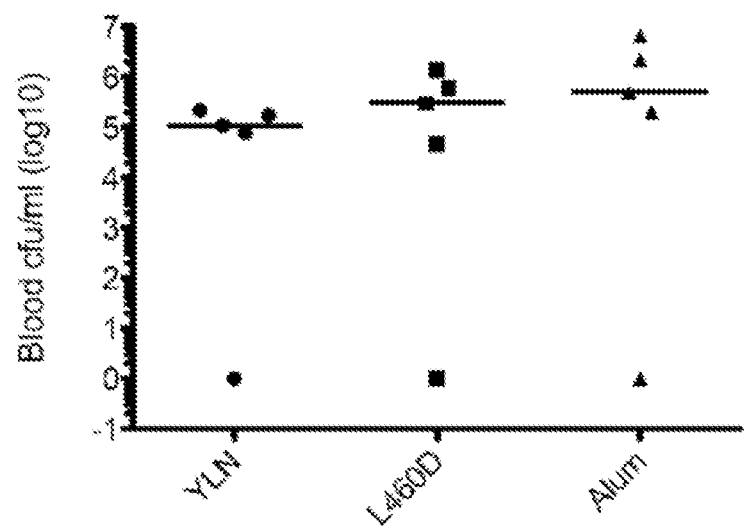
Figure 5D:
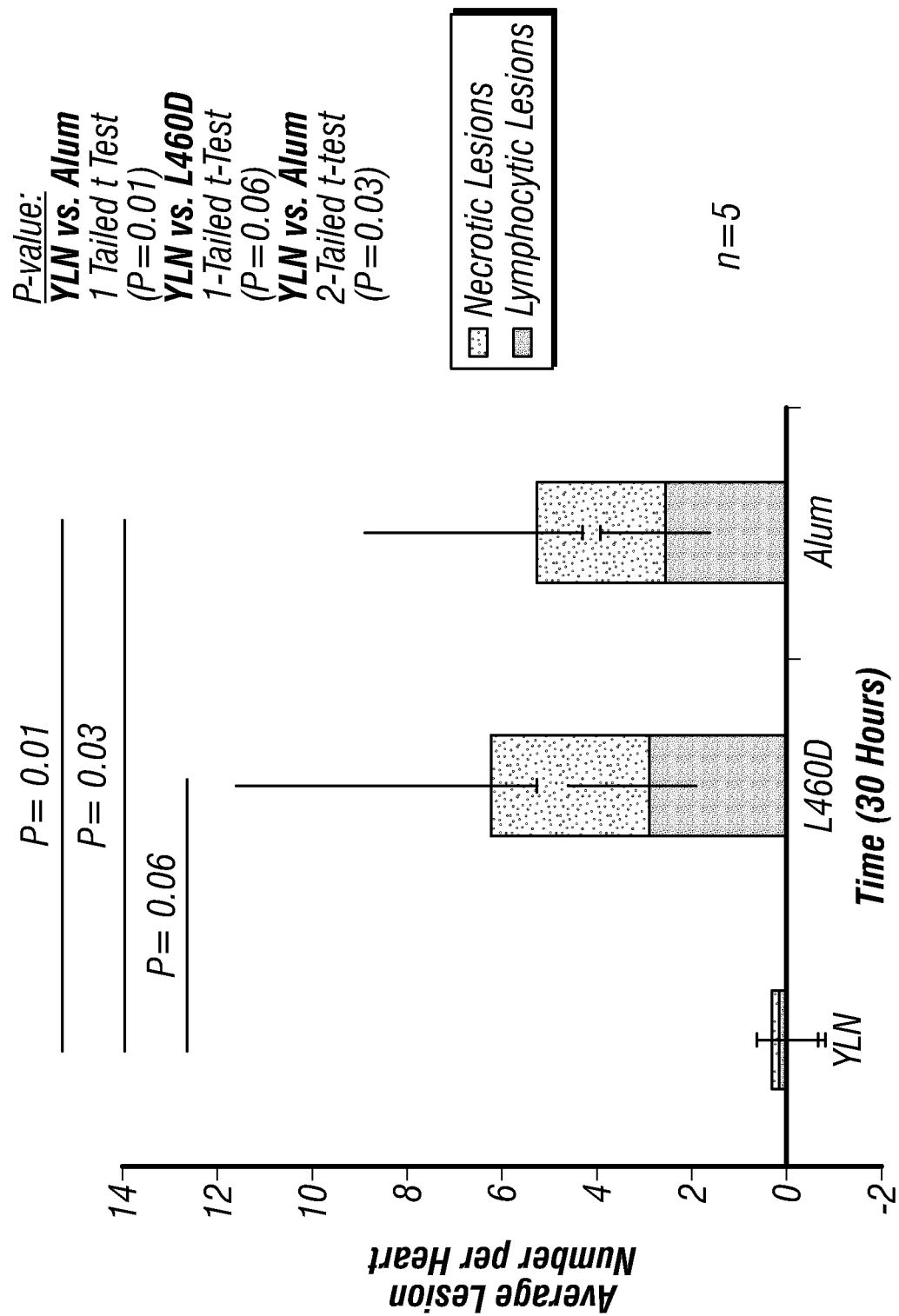

Given the observation that microlesion formation was CbpA/LR dependent and that microlesion formation was associated with the presence of pneumolysin, we immunized mice with YLN or control and tested for protection against lesion formation. Briefly, YLN is a recombinant construct composed of the pneumolysin toxoid L460D, flanked by the CbpA Laminin Receptor and Polymeric Immunoglobulin Receptor binding domains (FIG. 5A-B). Immunization of mice with the YLN construct, although it did not reduce bacterial titers (FIG. 5B), drastically reduced lesion formation in experimentally challenged mice (FIG. 5C). This stood in stark contrast to mice immunized with the L460D alone, which had lesion levels equivalent to alum control immunized mice (FIG. 5C).

All of the compositions and/or methods disclosed and claimed herein can be made and executed without undue experimentation in light of the present disclosure. While the compositions and methods of this invention have been described in terms of some embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bouche et al. *Vaccine*. 23:2074-2077, 2005.
Cundell & Tuomanen, *Microb Pathog*. 17:361-374, 1994.
Cundell, et al., *Nature*. 377:435-438, 1995.
Daniels et al. *Infection and Immunity* 78:2163-72, 2010.
El Kasmi et al., *J. Gen. Virol*. 81:729-735, 2000.

El Kasmi et al., *Mol. Immunol.* 35:905-918, 1998.
El Kasmi et al., *Vaccine.* 17:2436-2445, 1999
Idanpaan-Heikkila, et al., *J. Infect. Dis.* 176:704-712, 1997.
International Publication No. WO 05/108419
International Publication No. WO 05/108580
International Publication No. WO 90/006951
Jordan et al., *J. Am. Chem. Soc.* 128(28):9119-9128, 2006
Luo et al. *EMBO J.* 24(1):34-43, 2005.
McDaniel, et al. *Microb. Pathog.*, 13:261-269, 1992.
Obeid et al. *J. Virol.* 69:1420-1428, 1995.
Orihuela et al. *J Clin Invest.*, 119(6): 1638-1646, 2009.
Paton et al. *Infection and Immunity* 43:1085-1087, 1984.
PCT Application No. PCT/US97/07198
Radin et al., *Infect. Immun.* 73:7827-7835, 2005.
Ronda et al., *Eur. J. Biochem,* 164:621-624, 1987.
Saunders et al. *Infection and Immunity* 57:2547-2552, 1989.
Shapiro et al. *NJEM.* 325:1453, 1991.
Tuomanen et al. *NEJM* 322:1280-1284, 1995.
U.S. Pat. No. 6,042,838
U.S. Pat. No. 6,232,116
U.S. Pat. No. 6,858,706
U.S. Patent Publication 2009/0170162A1
U.S. Patent Publication 2009/0285846A1
U.S. Patent Publication 2010/0143394
U.S. Patent Publication 2010/0166795
Zhang et al., *Cell.* 102:827-837, 2000.
Zysk et al. *Infection and Immunity* 68:3740-3743, 2000.

The invention claimed is:

1. A method of reducing the formation or number of cardiac microlesions due to *Streptococcus pneumoniae* infection in a patient, the method comprising administering an effective amount of a composition to a patient, wherein the composition comprises an immunogenic fusion protein comprising a YPT fragment, a T-cell epitope, and a NEEK fragment, wherein said immunogenic fusion protein comprises SEQ ID NO: 8; and wherein said effective amount of said composition is administered intramuscularly, intranasally, intraperitoneally, subcutaneously, via inhalation, or via injection.

2. The method of claim 1, wherein the patient is immune deficient, is immunocompromised, is hospitalized, is undergoing an invasive medical procedure, is infected with influenza virus or is on a respirator.

3. The method of claim 1, wherein the effective amount of said immunogenic fusion protein comprises a concentration of 0.001 mg to 100 mg total per dose.

4. The method of claim 1, wherein the composition is administered in two or more doses, and wherein the interval of time between administration of doses is at least 2 weeks.

5. The method of claim 1, wherein the subject is further administered a composition comprising a second active agent, wherein the composition comprising the immunogenic polypeptide is administered at the same time as the composition comprising the second active agent.

6. The method of claim 1, wherein the subject is further administered a composition comprising a second active agent, wherein the composition comprising the immunogenic polypeptide is administered before or after the composition comprising the second active agent is administered, and wherein the interval of time between administration of composition comprising the immunogenic polypeptide and the composition comprising the second active agent is 1 to 30 days.

7. The method of claim 1, wherein the composition comprising the immunogenic polypeptide further comprises an antibacterial agent.

* * * * *

SEQUENCE LISTING

```
<160> NUMBER OF SEQ ID NOS: 14

<210> SEQ ID NO 1
<211> LENGTH: 116
<212> TYPE: PRT
<213> ORGANISM: Streptococcus pneumoniae

<400> SEQUENCE: 1

Met Pro Glu Lys Lys Val Ala Glu Ala Glu Lys Lys Val Glu Glu Ala
1               5                   10                  15

Lys Lys Lys Ala Glu Asp Gln Lys Glu Glu Asp Arg Arg Asn Tyr Pro
                20                  25                  30

Thr Asn Thr Tyr Lys Thr Leu Glu Leu Glu Ile Ala Glu Ser Asp Val
            35                  40                  45

Glu Val Lys Lys Ala Glu Leu Glu Leu Val Lys Glu Glu Ala Lys Glu
        50                  55                  60

Pro Arg Asn Glu Glu Lys Val Lys Gln Ala Lys Ala Glu Val Glu Ser
65                  70                  75                  80

Lys Lys Ala Glu Ala Thr Arg Leu Glu Lys Ile Lys Thr Asp Arg Lys
                85                  90                  95

Lys Ala Glu Glu Glu Ala Lys Arg Lys Ala Ala Glu Glu Asp Lys Val
                100                 105                 110

Lys Glu Lys Pro
        115

<210> SEQ ID NO 2
<211> LENGTH: 64
<212> TYPE: PRT
<213> ORGANISM: Streptococcus pneumoniae

<400> SEQUENCE: 2

Met Pro Glu Lys Lys Cys Ala Glu Ala Glu Lys Lys Val Glu Glu Ala
1               5                   10                  15

Lys Lys Lys Ala Glu Asp Gln Lys Glu Glu Asp Arg Arg Asn Tyr Pro
                20                  25                  30

Thr Asn Thr Tyr Lys Thr Leu Glu Leu Glu Ile Ala Glu Ser Asp Val
            35                  40                  45

Glu Val Lys Lys Ala Glu Leu Glu Leu Val Cys Glu Glu Ala Lys Glu
        50                  55                  60

<210> SEQ ID NO 3
<211> LENGTH: 84
<212> TYPE: PRT
<213> ORGANISM: Streptococcus pneumoniae

<400> SEQUENCE: 3
```

Met Asn Thr Tyr Cys Thr Leu Glu Leu Glu Ile Ala Glu Ser Asp Val
1               5                   10                  15

Glu Val Lys Lys Ala Glu Leu Glu Leu Val Lys Glu Ala Lys Glu
            20                  25                  30

Pro Arg Asn Glu Glu Lys Val Lys Gln Ala Lys Ala Glu Val Glu Ser
            35                  40                  45

Lys Lys Ala Glu Ala Thr Arg Leu Glu Lys Ile Lys Thr Asp Arg Lys
50                  55                  60

Lys Ala Glu Glu Glu Ala Lys Arg Lys Ala Ala Glu Glu Asp Lys Cys
65                  70                  75                  80

Lys Glu Lys Pro

<210> SEQ ID NO 4
<211> LENGTH: 44
<212> TYPE: PRT
<213> ORGANISM: Streptococcus pneumoniae

<400> SEQUENCE: 4

Gln Tyr Ile Lys Ala Asn Ser Lys Phe Ile Gly Ile Thr Gly Gly Ala
1               5                   10                  15

Cys Lys Lys Ala Glu Asp Gln Lys Glu Glu Asp Arg Arg Asn Tyr Pro
            20                  25                  30

Thr Asn Thr Tyr Lys Thr Leu Glu Leu Glu Cys Ala
            35                  40

<210> SEQ ID NO 5
<211> LENGTH: 45
<212> TYPE: PRT
<213> ORGANISM: Streptococcus pneumoniae

<400> SEQUENCE: 5

Gln Tyr Ile Lys Ala Asn Ser Lys Phe Ile Gly Ile Thr Gln Tyr Ile
1               5                   10                  15

Lys Ala Asn Ser Lys Phe Ile Gly Ile Thr Gly Gly Lys Glu Cys Ala
            20                  25                  30

Lys Glu Pro Arg Asn Glu Glu Lys Val Lys Gln Cys Lys
            35                  40                  45

<210> SEQ ID NO 6
<211> LENGTH: 31
<212> TYPE: PRT
<213> ORGANISM: Streptococcus pneumoniae

<400> SEQUENCE: 6

Met Ala Cys Lys Lys Ala Glu Asp Gln Lys Glu Glu Asp Arg Arg Asn
1               5                   10                  15

Tyr Pro Thr Asn Thr Tyr Lys Thr Leu Glu Leu Glu Cys Ala Glu
            20                  25                  30

<210> SEQ ID NO 7
<211> LENGTH: 17
<212> TYPE: PRT
<213> ORGANISM: Streptococcus pneumoniae

<400> SEQUENCE: 7

Lys Glu Cys Ala Lys Glu Pro Arg Asn Glu Glu Lys Val Lys Gln Cys
1               5                   10                  15

Lys

```
<210> SEQ ID NO 8
<211> LENGTH: 520
<212> TYPE: PRT
<213> ORGANISM: Streptococcus pneumoniae

<400> SEQUENCE: 8

Met Ala Cys Lys Lys Ala Glu Asp Gln Lys Glu Glu Asp Arg Arg Asn
1               5                   10                  15

Tyr Pro Thr Asn Thr Tyr Lys Thr Leu Glu Leu Glu Cys Ala Glu Gly
            20                  25                  30

Gly Ala Asn Lys Ala Val Asn Asp Phe Ile Leu Ala Met Asn Tyr Asp
        35                  40                  45

Lys Lys Lys Leu Leu Thr His Gln Gly Glu Ser Ile Glu Asn Arg Phe
    50                  55                  60

Ile Lys Glu Gly Asn Gln Leu Pro Asp Glu Phe Val Val Ile Glu Arg
65                  70                  75                  80

Lys Lys Arg Ser Leu Ser Thr Asn Thr Ser Asp Ile Ser Val Thr Ala
                85                  90                  95

Thr Asn Asp Ser Arg Leu Tyr Pro Gly Ala Leu Leu Val Asp Glu
            100                 105                 110

Thr Leu Leu Glu Asn Asn Pro Thr Leu Leu Ala Val Asp Arg Ala Pro
        115                 120                 125

Met Thr Tyr Ser Ile Asp Leu Pro Gly Leu Ala Ser Ser Asp Ser Phe
    130                 135                 140

Leu Gln Val Glu Asp Pro Ser Asn Ser Ser Val Arg Gly Ala Val Asn
145                 150                 155                 160

Asp Leu Leu Ala Lys Trp His Gln Asp Tyr Gly Gln Val Asn Asn Val
                165                 170                 175

Pro Ala Arg Met Gln Tyr Glu Lys Ile Thr Ala His Ser Met Glu Gln
            180                 185                 190

Leu Lys Val Lys Phe Gly Ser Asp Phe Glu Lys Thr Gly Asn Ser Leu
        195                 200                 205

Asp Ile Asp Phe Asn Ser Val His Ser Gly Glu Lys Gln Ile Gln Ile
    210                 215                 220

Val Asn Phe Lys Gln Ile Tyr Tyr Thr Val Ser Val Asp Ala Val Lys
225                 230                 235                 240

Asn Pro Gly Asp Val Phe Gln Asp Thr Val Thr Val Glu Asp Leu Lys
                245                 250                 255

Gln Arg Gly Ile Ser Ala Glu Arg Pro Leu Val Tyr Ile Ser Ser Val
            260                 265                 270

Ala Tyr Gly Arg Gln Val Tyr Leu Lys Leu Glu Thr Ser Lys Ser
        275                 280                 285

Asp Glu Val Glu Ala Ala Phe Glu Ala Leu Ile Lys Gly Val Lys Val
    290                 295                 300

Ala Pro Gln Thr Glu Trp Lys Gln Ile Leu Asp Asn Thr Glu Val Lys
305                 310                 315                 320

Ala Val Ile Leu Gly Gly Asp Pro Ser Ser Gly Ala Arg Val Thr
                325                 330                 335

Gly Lys Val Asp Met Val Glu Asp Leu Ile Gln Glu Gly Ser Arg Phe
            340                 345                 350

Thr Ala Asp His Pro Gly Leu Pro Ile Ser Tyr Thr Thr Ser Phe Leu
        355                 360                 365

Arg Asp Asn Val Val Ala Thr Phe Gln Asn Ser Thr Tyr Val Glu
    370                 375                 380
```

```
Thr Lys Val Thr Ala Tyr Arg Asn Gly Asp Leu Leu Leu Asp His Ser
385                 390                 395                 400

Gly Ala Tyr Val Ala Gln Tyr Tyr Ile Thr Trp Asp Glu Leu Ser Tyr
                405                 410                 415

Asp His Gln Gly Lys Glu Val Leu Thr Pro Lys Ala Trp Asp Arg Asn
            420                 425                 430

Gly Gln Asp Leu Thr Ala His Phe Thr Thr Ser Ile Pro Leu Lys Gly
        435                 440                 445

Asn Val Arg Asn Leu Ser Val Lys Ile Arg Glu Cys Thr Gly Leu Ala
    450                 455                 460

Trp Glu Trp Trp Arg Thr Val Tyr Glu Lys Thr Asp Leu Pro Leu Val
465                 470                 475                 480

Arg Lys Arg Thr Ile Ser Ile Trp Gly Thr Thr Asp Tyr Pro Gln Val
                485                 490                 495

Glu Asp Lys Val Glu Asn Asp Lys Glu Cys Ala Lys Glu Pro Arg Asn
            500                 505                 510

Glu Glu Lys Val Lys Gln Cys Lys
            515                 520

<210> SEQ ID NO 9
<211> LENGTH: 518
<212> TYPE: PRT
<213> ORGANISM: Streptococcus pneumoniae

<400> SEQUENCE: 9

Met Ala Cys Lys Lys Ala Glu Asp Gln Lys Glu Glu Asp Arg Arg Asn
1               5                   10                  15

Tyr Pro Thr Asn Thr Tyr Lys Thr Leu Glu Leu Glu Cys Ala Glu Gly
                20                  25                  30

Gly Ala Asn Lys Ala Val Asn Asp Phe Ile Leu Ala Met Asn Tyr Asp
            35                  40                  45

Lys Lys Lys Leu Leu Thr His Gln Gly Glu Ser Ile Glu Asn Arg Phe
50                  55                  60

Ile Lys Glu Gly Asn Gln Leu Pro Asp Glu Phe Val Val Ile Glu Arg
65                  70                  75                  80

Lys Lys Arg Ser Leu Ser Thr Asn Thr Ser Asp Ile Ser Val Thr Ala
                85                  90                  95

Thr Asn Asp Ser Arg Leu Tyr Pro Gly Ala Leu Leu Val Val Asp Glu
                100                 105                 110

Thr Leu Leu Glu Asn Asn Pro Thr Leu Leu Ala Val Asp Arg Ala Pro
            115                 120                 125

Met Thr Tyr Ser Ile Asp Leu Pro Gly Leu Ala Ser Ser Asp Ser Phe
130                 135                 140

Leu Gln Val Glu Asp Pro Ser Asn Ser Ser Val Arg Gly Ala Val Asn
145                 150                 155                 160

Asp Leu Leu Ala Lys Trp His Gln Asp Tyr Gly Gln Val Asn Asn Val
                165                 170                 175

Pro Met Gln Tyr Glu Lys Ile Thr Ala His Ser Met Glu Gln Leu Lys
            180                 185                 190

Val Lys Phe Gly Ser Asp Phe Lys Thr Gly Asn Ser Leu Asp Ile
        195                 200                 205

Asp Phe Asn Ser Val His Ser Gly Glu Lys Gln Ile Gln Ile Val Asn
    210                 215                 220

Phe Lys Gln Ile Tyr Tyr Thr Val Ser Val Asp Ala Val Lys Asn Pro
```

-continued

```
                225                 230                 235                 240
        Gly Asp Val Phe Gln Asp Thr Val Thr Val Glu Asp Leu Lys Gln Arg
                        245                 250                 255
        Gly Ile Ser Ala Glu Arg Pro Leu Val Tyr Ile Ser Ser Val Ala Tyr
                260                 265                 270
        Gly Arg Gln Val Tyr Leu Lys Leu Glu Thr Thr Ser Lys Ser Asp Glu
                        275                 280                 285
        Val Glu Ala Ala Phe Glu Ala Leu Ile Lys Gly Val Lys Val Ala Pro
                290                 295                 300
        Gln Thr Glu Trp Lys Gln Ile Leu Asp Asn Thr Glu Val Lys Ala Val
        305                 310                 315                 320
        Ile Leu Gly Gly Asp Pro Ser Ser Gly Ala Arg Val Val Thr Gly Lys
                        325                 330                 335
        Val Asp Met Val Glu Asp Leu Ile Gln Glu Gly Ser Arg Phe Thr Ala
                        340                 345                 350
        Asp His Pro Gly Leu Pro Ile Ser Tyr Thr Thr Ser Phe Leu Arg Asp
                        355                 360                 365
        Asn Val Val Ala Thr Phe Gln Asn Ser Thr Asp Tyr Val Glu Thr Lys
                370                 375                 380
        Val Thr Ala Tyr Arg Asn Gly Asp Leu Leu Leu Asp His Ser Gly Ala
        385                 390                 395                 400
        Tyr Val Ala Gln Tyr Tyr Ile Thr Trp Asp Glu Leu Ser Tyr Asn His
                        405                 410                 415
        Gln Gly Lys Glu Val Leu Thr Pro Lys Ala Trp Asp Arg Asn Gly Gln
                        420                 425                 430
        Asp Leu Thr Ala His Phe Thr Thr Ser Ile Pro Leu Lys Gly Asn Val
                        435                 440                 445
        Arg Asn Leu Ser Val Lys Ile Arg Glu Cys Thr Gly Leu Ala Trp Glu
                        450                 455                 460
        Trp Trp Arg Thr Val Tyr Glu Lys Thr Asp Leu Pro Leu Val Arg Lys
        465                 470                 475                 480
        Arg Thr Ile Ser Ile Trp Gly Thr Thr Leu Tyr Pro Gln Val Glu Asp
                        485                 490                 495
        Lys Val Glu Asn Asp Lys Glu Cys Ala Lys Glu Pro Arg Asn Glu Glu
                        500                 505                 510
        Lys Val Lys Gln Cys Lys
                        515

<210> SEQ ID NO 10
<211> LENGTH: 520
<212> TYPE: PRT
<213> ORGANISM: Streptococcus pneumoniae

<400> SEQUENCE: 10

Met Ala Cys Lys Lys Ala Glu Asp Gln Lys Glu Glu Asp Arg Arg Asn
        1               5                   10                  15
        Tyr Pro Thr Asn Thr Tyr Lys Thr Leu Glu Leu Glu Cys Ala Glu Gly
                        20                  25                  30
        Gly Ala Asn Lys Ala Val Asn Asp Phe Ile Leu Ala Met Asn Tyr Asp
                35                  40                  45
        Lys Lys Lys Leu Leu Thr His Gln Gly Glu Ser Ile Glu Asn Arg Phe
                50                  55                  60
        Ile Lys Glu Gly Asn Gln Leu Pro Asp Glu Phe Val Val Ile Glu Arg
        65                  70                  75                  80
```

```
Lys Lys Arg Ser Leu Ser Thr Asn Thr Ser Asp Ile Ser Val Thr Ala
                 85                  90                  95

Thr Asn Asp Ser Arg Leu Tyr Pro Gly Ala Leu Leu Val Val Asp Glu
            100                 105                 110

Thr Leu Leu Glu Asn Asn Pro Thr Leu Leu Ala Val Asp Arg Ala Pro
            115                 120                 125

Met Thr Tyr Ser Ile Asp Leu Pro Gly Leu Ala Ser Ser Asp Ser Phe
            130                 135                 140

Leu Gln Val Glu Asp Pro Ser Asn Ser Ser Val Arg Gly Ala Val Asn
145                 150                 155                 160

Asp Leu Leu Ala Lys Trp His Gln Asp Tyr Gly Gln Val Asn Asn Val
                165                 170                 175

Pro Ala Arg Met Gln Tyr Glu Lys Ile Thr Ala His Ser Met Glu Gln
                180                 185                 190

Leu Lys Val Lys Phe Gly Ser Asp Phe Glu Lys Thr Gly Asn Ser Leu
            195                 200                 205

Asp Ile Asp Phe Asn Ser Val His Ser Gly Lys Gln Ile Gln Ile
            210                 215                 220

Val Asn Phe Lys Gln Ile Tyr Tyr Thr Val Ser Val Asp Ala Val Lys
225                 230                 235                 240

Asn Pro Gly Asp Val Phe Gln Asp Thr Val Thr Val Glu Asp Leu Lys
                245                 250                 255

Gln Arg Gly Ile Ser Ala Glu Arg Pro Leu Val Tyr Ile Ser Ser Val
            260                 265                 270

Ala Tyr Gly Arg Gln Val Tyr Leu Lys Leu Glu Thr Ser Lys Ser
            275                 280                 285

Asp Glu Val Glu Ala Ala Phe Glu Ala Leu Ile Lys Gly Val Lys Val
290                 295                 300

Ala Pro Gln Thr Glu Trp Lys Gln Ile Leu Asp Asn Thr Glu Val Lys
305                 310                 315                 320

Ala Val Ile Leu Gly Gly Asp Pro Ser Ser Gly Ala Arg Val Val Thr
            325                 330                 335

Gly Lys Val Asp Met Val Glu Asp Leu Ile Gln Glu Gly Ser Arg Phe
            340                 345                 350

Thr Ala Asp His Pro Gly Leu Pro Ile Ser Tyr Thr Thr Ser Phe Leu
            355                 360                 365

Arg Asp Asn Val Val Ala Thr Phe Gln Asn Ser Thr Asp Tyr Val Glu
            370                 375                 380

Thr Lys Val Thr Ala Tyr Arg Asn Gly Asp Leu Leu Leu Asp His Ser
385                 390                 395                 400

Gly Ala Tyr Val Ala Gln Tyr Tyr Ile Thr Trp Asp Glu Leu Ser Tyr
                405                 410                 415

Asn His Gln Gly Lys Glu Val Leu Thr Pro Lys Ala Trp Asp Arg Asn
            420                 425                 430

Gly Gln Asp Leu Thr Ala His Phe Thr Thr Ser Ile Pro Leu Lys Gly
            435                 440                 445

Asn Val Arg Asn Leu Ser Val Lys Ile Arg Glu Gly Thr Gly Leu Ala
450                 455                 460

Phe Glu Trp Trp Arg Thr Val Tyr Glu Lys Thr Asp Leu Pro Leu Val
465                 470                 475                 480

Arg Lys Arg Thr Ile Ser Ile Trp Gly Thr Thr Leu Tyr Pro Gln Val
                485                 490                 495

Glu Asp Lys Val Glu Asn Asp Lys Glu Cys Ala Lys Glu Pro Arg Asn
```

```
                500                 505                 510
Glu Glu Lys Val Lys Gln Cys Lys
        515                 520

<210> SEQ ID NO 11
<211> LENGTH: 503
<212> TYPE: PRT
<213> ORGANISM: Streptococcus pneumoniae

<400> SEQUENCE: 11

Met Ala Cys Lys Lys Ala Glu Asp Gln Lys Glu Asp Arg Arg Asn
1               5                   10                  15

Tyr Pro Thr Asn Thr Tyr Lys Thr Leu Glu Leu Glu Cys Ala Glu Gly
                20                  25                  30

Gly Ala Asn Lys Ala Val Asn Asp Phe Ile Leu Ala Met Asn Tyr Asp
            35                  40                  45

Lys Lys Lys Leu Leu Thr His Gln Gly Glu Ser Ile Glu Asn Arg Phe
        50                  55                  60

Ile Lys Glu Gly Asn Gln Leu Pro Asp Glu Phe Val Val Ile Glu Arg
65                  70                  75                  80

Lys Lys Arg Ser Leu Ser Thr Asn Thr Ser Asp Ile Ser Val Thr Ala
                85                  90                  95

Thr Asn Asp Ser Arg Leu Tyr Pro Gly Ala Leu Leu Val Val Asp Glu
                100                 105                 110

Thr Leu Leu Glu Asn Asn Pro Thr Leu Leu Ala Val Asp Arg Ala Pro
        115                 120                 125

Met Thr Tyr Ser Ile Asp Leu Pro Gly Leu Ala Ser Ser Asp Ser Phe
130                 135                 140

Leu Gln Val Glu Asp Pro Ser Asn Ser Ser Val Arg Gly Ala Val Asn
145                 150                 155                 160

Asp Leu Leu Ala Lys Trp His Gln Asp Tyr Gly Gln Val Asn Asn Val
                165                 170                 175

Pro Ala Arg Met Gln Tyr Glu Lys Ile Thr Ala His Ser Met Glu Gln
            180                 185                 190

Leu Lys Val Lys Phe Gly Ser Asp Phe Glu Lys Thr Gly Asn Ser Leu
        195                 200                 205

Asp Ile Asp Phe Asn Ser Val His Ser Gly Glu Lys Gln Ile Gln Ile
210                 215                 220

Val Asn Phe Lys Gln Ile Tyr Tyr Thr Val Ser Val Asp Ala Val Lys
225                 230                 235                 240

Asn Pro Gly Asp Val Phe Gln Asp Thr Val Thr Val Glu Asp Leu Lys
                245                 250                 255

Gln Arg Gly Ile Ser Ala Glu Arg Pro Leu Val Tyr Ile Ser Ser Val
            260                 265                 270

Ala Tyr Gly Arg Gln Val Tyr Leu Lys Leu Glu Thr Thr Ser Lys Ser
        275                 280                 285

Asp Glu Val Glu Ala Ala Phe Glu Ala Leu Ile Lys Gly Val Lys Val
        290                 295                 300

Ala Pro Gln Thr Glu Trp Lys Gln Ile Leu Asp Asn Thr Glu Val Lys
305                 310                 315                 320

Ala Val Ile Leu Gly Gly Asp Pro Ser Ser Gly Ala Arg Val Val Thr
                325                 330                 335

Gly Lys Val Asp Met Val Glu Asp Leu Ile Gln Glu Gly Ser Arg Phe
            340                 345                 350
```

```
Thr Ala Asp His Pro Gly Leu Pro Ile Ser Tyr Thr Thr Ser Phe Leu
            355                 360                 365

Arg Asp Asn Val Val Ala Thr Phe Gln Asn Ser Thr Asp Tyr Val Glu
    370                 375                 380

Thr Lys Val Thr Ala Tyr Arg Asn Gly Asp Leu Leu Leu Asp His Ser
385                 390                 395                 400

Gly Ala Tyr Val Ala Gln Tyr Tyr Ile Thr Trp Asp Glu Leu Ser Tyr
                405                 410                 415

Asp His Gln Gly Lys Glu Val Leu Thr Pro Lys Ala Trp Asp Arg Asn
            420                 425                 430

Gly Gln Asp Leu Thr Ala His Phe Thr Thr Ser Ile Pro Leu Lys Gly
        435                 440                 445

Asn Val Arg Asn Leu Ser Val Lys Ile Arg Glu Cys Thr Gly Leu Ala
    450                 455                 460

Trp Glu Trp Trp Arg Thr Val Tyr Glu Lys Thr Asp Leu Pro Leu Val
465                 470                 475                 480

Arg Lys Arg Thr Ile Ser Ile Trp Gly Thr Thr Asp Tyr Pro Gln Val
                485                 490                 495

Glu Asp Lys Val Glu Asn Asp
            500

<210> SEQ ID NO 12
<211> LENGTH: 488
<212> TYPE: PRT
<213> ORGANISM: Streptococcus pneumoniae

<400> SEQUENCE: 12

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220
```

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
    290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
                340                 345                 350

Thr Lys Val Thr Ala Tyr Arg Asn Gly Asp Leu Leu Leu Asp His Ser
            355                 360                 365

Gly Ala Tyr Val Ala Gln Tyr Tyr Ile Thr Trp Asp Glu Leu Ser Tyr
    370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
                420                 425                 430

Trp Glu Trp Trp Arg Thr Val Tyr Glu Lys Thr Asp Leu Pro Leu Val
            435                 440                 445

Arg Lys Arg Thr Ile Ser Ile Trp Gly Thr Thr Asp Tyr Pro Gln Val
        450                 455                 460

Glu Asp Lys Val Glu Asn Asp Lys Glu Cys Ala Lys Glu Pro Arg Asn
465                 470                 475                 480

Glu Glu Lys Val Lys Gln Cys Lys
                485

<210> SEQ ID NO 13
<211> LENGTH: 503
<212> TYPE: PRT
<213> ORGANISM: Streptococcus pneumoniae

<400> SEQUENCE: 13

Met Ala Cys Lys Lys Ala Glu Asp Gln Lys Glu Glu Asp Arg Arg Asn
1               5                   10                  15

Tyr Pro Thr Asn Thr Tyr Lys Thr Leu Glu Leu Glu Cys Ala Glu Gly
                20                  25                  30

Gly Ala Asn Lys Ala Val Asn Asp Phe Ile Leu Ala Met Asn Tyr Asp
            35                  40                  45

Lys Lys Lys Leu Leu Thr His Gln Gly Glu Ser Ile Glu Asn Arg Phe
        50                  55                  60

Ile Lys Glu Gly Asn Gln Leu Pro Asp Glu Phe Val Val Ile Glu Arg
65                  70                  75                  80

Lys Lys Arg Ser Leu Ser Thr Asn Thr Ser Asp Ile Ser Val Thr Ala
                85                  90                  95

Thr Asn Asp Ser Arg Leu Tyr Pro Gly Ala Leu Leu Val Val Asp Glu

-continued

```
                100                 105                 110
Thr Leu Leu Glu Asn Asn Pro Thr Leu Leu Ala Val Asp Arg Ala Pro
            115                 120                 125
Met Thr Tyr Ser Ile Asp Leu Pro Gly Leu Ala Ser Ser Asp Ser Phe
        130                 135                 140
Leu Gln Val Glu Asp Pro Ser Asn Ser Ser Val Arg Gly Ala Val Asn
145                 150                 155                 160
Asp Leu Leu Ala Lys Trp His Gln Asp Tyr Gly Gln Val Asn Asn Val
                165                 170                 175
Pro Ala Arg Met Gln Tyr Glu Lys Ile Thr Ala His Ser Met Glu Gln
            180                 185                 190
Leu Lys Val Lys Phe Gly Ser Asp Phe Glu Lys Thr Gly Asn Ser Leu
        195                 200                 205
Asp Ile Asp Phe Asn Ser Val His Ser Gly Lys Gln Ile Gln Ile
    210                 215                 220
Val Asn Phe Lys Gln Ile Tyr Tyr Thr Val Ser Val Asp Ala Val Lys
225                 230                 235                 240
Asn Pro Gly Asp Val Phe Gln Asp Thr Val Thr Val Glu Asp Leu Lys
                245                 250                 255
Gln Arg Gly Ile Ser Ala Glu Arg Pro Leu Val Tyr Ile Ser Ser Val
            260                 265                 270
Ala Tyr Gly Arg Gln Val Tyr Leu Lys Leu Glu Thr Ser Lys Ser
        275                 280                 285
Asp Glu Val Glu Ala Ala Phe Glu Ala Leu Ile Lys Gly Val Lys Val
    290                 295                 300
Ala Pro Gln Thr Glu Trp Lys Gln Ile Leu Asp Asn Thr Glu Val Lys
305                 310                 315                 320
Ala Val Ile Leu Gly Gly Asp Pro Ser Ser Gly Ala Arg Val Val Thr
                325                 330                 335
Gly Lys Val Asp Met Val Glu Asp Leu Ile Gln Glu Gly Ser Arg Phe
            340                 345                 350
Thr Ala Asp His Pro Gly Leu Pro Ile Ser Tyr Thr Thr Ser Phe Leu
        355                 360                 365
Arg Asp Asn Val Val Ala Thr Phe Gln Asn Ser Thr Asp Tyr Val Glu
    370                 375                 380
Thr Lys Val Thr Ala Tyr Arg Asn Gly Asp Leu Leu Leu Asp His Ser
385                 390                 395                 400
Gly Ala Tyr Val Ala Gln Tyr Tyr Ile Thr Trp Asp Glu Leu Ser Tyr
                405                 410                 415
Asn His Gln Gly Lys Glu Val Leu Thr Pro Lys Ala Trp Asp Arg Asn
            420                 425                 430
Gly Gln Asp Leu Thr Ala His Phe Thr Thr Ser Ile Pro Leu Lys Gly
        435                 440                 445
Asn Val Arg Asn Leu Ser Val Lys Ile Arg Glu Gly Thr Gly Leu Ala
    450                 455                 460
Phe Glu Trp Trp Arg Thr Val Tyr Glu Lys Thr Asp Leu Pro Leu Val
465                 470                 475                 480
Arg Lys Arg Thr Ile Ser Ile Trp Gly Thr Thr Leu Tyr Pro Gln Val
                485                 490                 495
Glu Asp Lys Val Glu Asn Asp
            500

<210> SEQ ID NO 14
```

<211> LENGTH: 488
<212> TYPE: PRT
<213> ORGANISM: Streptococcus pneumoniae

<400> SEQUENCE: 14

```
Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
    290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Asp His Ser
        355                 360                 365

Gly Ala Tyr Val Ala Gln Tyr Tyr Ile Thr Trp Asp Glu Leu Ser Tyr
    370                 375                 380

Asn His Gln Gly Lys Glu Val Leu Thr Pro Lys Ala Trp Asp Arg Asn
```

-continued

```
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Gly Thr Gly Leu Ala
            420                 425                 430

Phe Glu Trp Trp Arg Thr Val Tyr Glu Lys Thr Asp Leu Pro Leu Val
        435                 440                 445

Arg Lys Arg Thr Ile Ser Ile Trp Gly Thr Thr Leu Tyr Pro Gln Val
    450                 455                 460

Glu Asp Lys Val Glu Asn Asp Lys Glu Cys Ala Lys Glu Pro Arg Asn
465                 470                 475                 480

Glu Glu Lys Val Lys Gln Cys Lys
                485
```